(12) United States Patent
Stahmann et al.

(10) Patent No.: US 7,720,541 B2
(45) Date of Patent: May 18, 2010

(54) ADAPTIVE THERAPY FOR DISORDERED BREATHING

(75) Inventors: Jeffrey E. Stahmann, Ramsey, MN (US); John D. Hatlestad, Maplewood, MN (US); Quan Ni, Shoreview, MN (US); Jesse Hartley, Lino Lakes, MN (US); Douglas R. Daum, Oakdale, MN (US); Kent Lee, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2018 days.

(21) Appl. No.: 10/643,203

(22) Filed: Aug. 18, 2003

(65) Prior Publication Data

US 2005/0039745 A1 Feb. 24, 2005

(51) Int. Cl.
*A61N 1/00* (2006.01)
(52) U.S. Cl. ........................................................ 607/42
(58) Field of Classification Search .................. 607/20, 607/42, 17, 2; 600/534–543
See application file for complete search history.

(56) References Cited

U.S. PATENT DOCUMENTS

| | | | |
|---|---|---|---|
| 4,365,636 A * | 12/1982 | Barker | 600/529 |
| 4,813,427 A | 3/1989 | Schlaefke et al. | |
| 4,827,935 A | 5/1989 | Geddes et al. | |
| 4,830,008 A | 5/1989 | Meer | |
| 4,856,524 A | 8/1989 | Baker, Jr. | |
| 5,024,222 A | 6/1991 | Thacker | |
| 5,105,354 A | 4/1992 | Nishimura | |
| 5,123,425 A | 6/1992 | Shannon, Jr. et al. | |
| 5,146,918 A | 9/1992 | Kallok et al. | |
| 5,178,156 A | 1/1993 | Takishima et al. | |
| 5,211,173 A | 5/1993 | Kallok et al. | |
| 5,215,082 A | 6/1993 | Kallok et al. | |
| 5,233,983 A | 8/1993 | Markowitz | |
| 5,335,657 A | 8/1994 | Terry, Jr. et al. | |
| 5,466,245 A | 11/1995 | Spinelli et al. | |
| 5,483,969 A | 1/1996 | Testerman et al. | |
| 5,485,851 A | 1/1996 | Erickson | |
| 5,522,862 A | 6/1996 | Testerman et al. | |
| 5,549,655 A | 8/1996 | Erickson | |

(Continued)

FOREIGN PATENT DOCUMENTS

EP 0750920 1/1997

(Continued)

OTHER PUBLICATIONS

Bradley et al., Sleep Apnea and Heart Failure, Park I: Obstructive Sleep Apnea, 107 Circulation 1671-1678 (2003).

(Continued)

*Primary Examiner*—Mark W Bockelman
*Assistant Examiner*—Roland Dinga
(74) *Attorney, Agent, or Firm*—Hollingsworth & Funk, LLC

(57) ABSTRACT

An approach to providing disordered breathing therapy includes detecting disordered breathing and adapting a therapy to mitigate the disordered breathing. The therapy may be adapted to enhance therapy effectiveness, to provide therapy that reduces an impact of the therapy on the patient, or to achieve other therapeutic goals. Cardiac electrical therapy to mitigate the disordered breathing may include various cardiac pacing regimens and/or delivery of non-excitatory electrical stimulation to the heart.

38 Claims, 17 Drawing Sheets

U.S. PATENT DOCUMENTS

| | | | |
|---|---|---|---|
| 5,645,570 A | 7/1997 | Corbucci | |
| 5,713,933 A | 2/1998 | Condie et al. | |
| 5,738,102 A | 4/1998 | Lemelson | |
| 5,792,188 A | 8/1998 | Starkweather et al. | |
| 5,802,188 A | 9/1998 | McDonough | |
| 5,844,680 A | 12/1998 | Sperling | |
| 5,861,011 A | 1/1999 | Stoop | |
| 5,891,023 A | 4/1999 | Lynn | |
| 5,911,218 A | 6/1999 | DiMarco | |
| 5,944,680 A | 8/1999 | Christopherson et al. | |
| 5,970,975 A | 10/1999 | Estes et al. | |
| 6,064,910 A | 5/2000 | Andersson et al. | |
| 6,099,479 A | 8/2000 | Christopherson et al. | |
| 6,120,441 A | 9/2000 | Griebel | |
| 6,126,611 A * | 10/2000 | Bourgeois et al. | 600/529 |
| 6,128,534 A | 10/2000 | Park et al. | |
| 6,132,384 A | 10/2000 | Christopherson et al. | |
| 6,141,590 A | 10/2000 | Renirie et al. | |
| 6,221,011 B1 | 4/2001 | Bardy | |
| 6,240,316 B1 | 5/2001 | Richmond et al. | |
| 6,251,126 B1 | 6/2001 | Ottenhoff et al. | |
| 6,269,269 B1 | 7/2001 | Ottenhoff et al. | |
| 6,270,457 B1 | 8/2001 | Bardy | |
| 6,272,377 B1 | 8/2001 | Sweeney | |
| 6,275,727 B1 | 8/2001 | Hopper et al. | |
| 6,277,072 B1 | 8/2001 | Bardy | |
| 6,292,693 B1 * | 9/2001 | Darvish et al. | 607/9 |
| 6,312,378 B1 | 11/2001 | Bardy | |
| 6,336,903 B1 | 1/2002 | Bardy | |
| 6,363,270 B1 | 3/2002 | Colla et al. | |
| 6,398,728 B1 | 6/2002 | Bardy | |
| 6,415,183 B1 | 7/2002 | Scheiner et al. | |
| 6,459,929 B1 | 10/2002 | Hopper et al. | |
| 6,477,420 B1 * | 11/2002 | Struble et al. | 607/14 |
| 6,480,733 B1 | 11/2002 | Turcott | |
| 6,574,507 B1 | 6/2003 | Bonnet | |
| 6,580,944 B1 | 6/2003 | Katz et al. | |
| 6,589,188 B1 | 7/2003 | Street et al. | |
| 6,641,542 B2 | 11/2003 | Cho et al. | |
| 6,741,885 B1 | 5/2004 | Park et al. | |
| 6,752,765 B1 | 6/2004 | Jensen et al. | |
| 6,752,766 B2 | 6/2004 | Kowallik et al. | |
| 6,773,404 B2 | 8/2004 | Poezevera | |
| 6,810,287 B2 | 10/2004 | Zhu et al. | |
| 6,881,192 B1 | 4/2005 | Park | |
| 6,904,320 B2 | 6/2005 | Park et al. | |
| 6,928,324 B2 | 8/2005 | Park et al. | |
| 6,988,498 B2 | 1/2006 | Berthon-Jones et al. | |
| 7,155,278 B2 | 12/2006 | King et al. | |
| 2002/0193697 A1 * | 12/2002 | Cho et al. | 600/529 |
| 2003/0055461 A1 | 3/2003 | Girouard et al. | |
| 2003/0153953 A1 * | 8/2003 | Park et al. | 607/17 |
| 2003/0153954 A1 * | 8/2003 | Park et al. | 607/17 |
| 2003/0153955 A1 | 8/2003 | Park et al. | |
| 2003/0153956 A1 | 8/2003 | Park et al. | |
| 2003/0195571 A1 * | 10/2003 | Burnes et al. | 607/9 |
| 2003/0199945 A1 | 10/2003 | Ciulla | |
| 2003/0204213 A1 | 10/2003 | Jensen et al. | |
| 2003/0216789 A1 | 11/2003 | Deem et al. | |
| 2004/0002742 A1 * | 1/2004 | Florio | 607/19 |
| 2004/0030362 A1 | 2/2004 | Hill et al. | |
| 2004/0088027 A1 | 5/2004 | Burnes et al. | |
| 2004/0116981 A1 | 6/2004 | Mazar | |
| 2004/0122488 A1 | 6/2004 | Mazar et al. | |
| 2004/0128161 A1 | 7/2004 | Mazar et al. | |
| 2004/0133079 A1 | 7/2004 | Mazar et al. | |
| 2004/0138719 A1 | 7/2004 | Cho et al. | |
| 2004/0176809 A1 | 9/2004 | Cho et al. | |
| 2004/0186523 A1 * | 9/2004 | Florio | 607/17 |
| 2005/0039745 A1 | 2/2005 | Stahmann et al. | |
| 2005/0042589 A1 | 2/2005 | Hatlestad et al. | |
| 2005/0043644 A1 | 2/2005 | Stahmann et al. | |
| 2005/0043772 A1 | 2/2005 | Stahmann et al. | |

FOREIGN PATENT DOCUMENTS

| | | |
|---|---|---|
| EP | 0770407 | 5/1997 |
| EP | 0940155 | 8/1999 |
| EP | 1151718 | 7/2001 |
| EP | 1 172 125 A1 | 1/2002 |
| EP | 1317943 | 11/2003 |
| WO | 8402080 | 6/1984 |
| WO | 9203983 | 3/1992 |
| WO | WO9904841 | 2/1999 |
| WO | 00/01438 | 1/2000 |
| WO | 00/17615 | 3/2000 |
| WO | WO0017615 | 3/2000 |

OTHER PUBLICATIONS

Olusola et al., Nightcap: Laboratory and home-based evaluation of a portable sleep monitor, 32 Psychophysiology, 32-98 (1995). Abstract only.

Verrier et al., Sleep, dreams, and sudden death: the case for sleep as an autonomic stress test for the heart, 31 Cardiovascular Research 181-211 (1996).

Verrier et al., Sleep Related Cardiovascular Risk: New Home-Based Monitoring Technology for Improved Diagnosis and Therapy, 2 A.N. E. 158-175 (1997).

Young, T., Palta, M., Dempsey, J., Skatrud, J., Weber, S., and Badr, R., "The Occurrence of Sleep-Disordered Breathing Among Middle Aged Adults." *New England Journal of Medicine* (1993), 1230-5.

Javaheri, S., Parker, T.J., Liming, J.D., Corbett, W.S., Nishiyama, H., Wexler, L., and Roselle, G.A., "*Sleep Apnea in 81 Ambulatory Male Patients with Stable Heart Failure: Types and Their Prevalences, Consequences, and Presentations*." Circulation 97, No. 21 (1998), 2154-59.

Bradley, R.D. and Floras, J.S., "*Pathophysiologic and Therapeutic Implications of Sleep Apnea in Congestive Heart Failure*."J Cardiac Failure 2, No. 3 (1996), 223-40.

Balaban, K., Cho, Y., Mongeon, L., Liu, L., Foldvary, N., Burgess, R. and Scharf, C., "*Feasibility of Screening for Sleep Apnea Using Pacemaker Impedance Sensor*."NASPE 2001.

Garrigue, S., Bordier, P., Hocini, M., Jais, P., Haissaguerre, M., and Clementy, J., "*Night Atrial Overdrive with DDD Pacing Results in a Significant Reduction of Sleep Apnea Episodes and QOL Improvement in Heart Failure Patients*." NASPE 2001.

Jais, P., Haissaguerre, M., Clementry, J. "*Night Atrial Overdrive with DDD Pacing: a New Therapy for Sleep Apnea Syndrome*."NASPE 2000.

Hilton, M.F., Bates, R.A., Godfery, K.R., Chappell, M.J. and Cayton, R.M., "*Evaluation of Frequency and Time-frequency Spectral Analysis of Heart Rate Variability as a Diagnostic Marker of the Sleep Apnea Syndrome*." Med Biol Eng Comput Nov. 1999, 37(6), 760-9.

Roche, F., Gaspoz, J.M., Court-Fortune, I., Minini, P., Pichot, V., Duvermney, D., Costes, F., Lacour, J.R., Barthelemy and J.C., "*Screening of Obstructive Sleep Apnea Syndrome by Heart Rate Variability Analysis*." Circulation Sep. 28, 1999; 100(13):1411-5.

Vanninen, E., Tuunainen, A., Kansanen, M., Uusitupa, M. and Lansimies, E., "*Cardiac Sympathovagal Balance During Sleep Apnea Episodes*."Clin Physiol May 1996; 16(3):209-16.

Shahrokh, Javaheri, "*A Mechanism of Central Sleep Apnea In Patients With Heart Failure*." New England Journal of Medicine, Sep. 1999; 341(13):949-54.

Bradley, T.D., MD, Floras, J.S., MD, DPhil, *Sleep Apnea and Heart Failure, Park I: Obstructive Sleep Apnea*, Circulation, 2003; 107: 1671-1678.

Garrigue, S., MD et al., *Benefit of Atrial Pacing in Sleep Apnea Syndrome*, N. Engl. J. Med., vol. 346, No. 6, pp. 404-412 (Feb. 7, 2002).

Waldemark, Karina et al., *Detection of Apnea using Short Window FFT Technique and Artificial Neural Network*, SPIE, International Society for Optical Engineering, vol. 3390, pp. 122-133 (1998).

U.S. Appl. No. 10/269,611, filed Oct. 11, 2002, Hatlestad.

U.S. Appl. No. 10/309,770, filed Dec. 4, 2002, Ni et al.

U.S. Appl. No. 10/309,771, filed Dec. 4, 2002, Ni et al.
U.S. Appl. No. 10/642,998, filed Aug. 18, 2003, Hatlestad.
U.S. Appl. No. 10/643,006, filed Aug. 18, 2003, Lovett et al.
U.S. Appl. No. 10/643,016, filed Aug. 18, 2003, Stahmann et al.
U.S. Appl. No. 10/643,154, filed Aug. 18, 2003, Stahmann et al.
U.S. Appl. No. 11/717,561, filed Jul. 12, 2007, Ni et al.
U.S. Appl. No. 11/890,404, filed Aug. 6, 2007, Ni et al.

* cited by examiner

ADAPTIVE THERAPY FOR DISORDERED BREATHING

FIELD OF THE INVENTION

The present invention relates generally to an adaptive cardiac electrical therapy for disordered breathing.

BACKGROUND OF THE INVENTION

Disordered breathing may be caused by a wide spectrum of respiratory conditions involving the disruption of the normal respiratory cycle. Although disordered breathing often occurs during sleep, the condition may also occur while the patient is awake. Respiratory disruption can be particularly serious for patients concurrently suffering from cardiovascular deficiencies, such as congestive heart failure. Unfortunately, disordered breathing is often undiagnosed. If left untreated, the effects of disordered breathing may result in serious health consequences for the patient.

Various types of disordered respiration have been identified, including, for example, apnea, hypopnea, dyspnea, hyperpnea, tachypnea, and periodic breathing, including Cheyne-Stokes respiration (CSR). Apnea is a fairly common disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer.

In addition to apnea, other types of disordered respiration cycles have been identified, including hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Periodic breathing is characterized by cyclic respiratory patterns that may exhibit rhythmic rises and falls in tidal volume. Cheyne-Stokes respiration is a specific form of periodic breathing wherein the tidal volume decreases to zero resulting in apneic intervals. The breathing interruptions of periodic breathing and CSR may be associated with central apnea, or may be obstructive in nature. CSR is frequently observed in patients with congestive heart failure (CHF) and is associated with an increased risk of accelerated CHF progression. Because of the cardiovascular implications, therapy for respiration-related sleep disorders is of particular interest.

SUMMARY OF THE INVENTION

Various embodiments of the present invention involve methods and systems for providing an adaptive therapy for disordered breathing.

In accordance with an embodiment of the invention, an automated method for providing disordered breathing therapy involves detecting disordered breathing and adapting a cardiac electrical therapy to mitigate the disordered breathing. The adapted therapy is delivered to the patient. At least one of detecting the disordered breathing, adapting the therapy to mitigate the disordered breathing, and delivering the therapy is performed at least in part implantably.

In accordance with a further embodiment of the invention, an automated method of providing disordered breathing therapy involves detecting disordered breathing and delivering a cardiac electrical therapy to mitigate the disordered breathing. The effectiveness of the therapy is assessed and therapy is adapted to enhance therapy efficacy. At least one of detecting the disordered breathing, delivering the therapy, evaluating the therapy, and adapting the therapy to enhance effectiveness, is performed at least in part implantably.

In accordance with yet another embodiment of the invention, an automated method for providing disordered breathing involves detecting disordered breathing and adapting a cardiac electrical therapy to mitigate the disordered breathing while adjusting an impact of the therapy on the patient. At least one of detecting the disordered breathing and adapting the therapy to mitigate the disordered breathing is performed at least in part implantably.

Yet another embodiment of the invention includes an automated medical device for providing disordered breathing therapy. The medical device includes a detector system configured to detect patient conditions. A disordered breathing detection system is coupled to the detector system and is configured to detect disordered breathing. A therapy control module is coupled to the disordered breathing detector system and is configured to adapt a cardiac electrical therapy to mitigate the disordered breathing. A therapy delivery system, coupled to the therapy control module, is configured to deliver the adapted therapy to the patient. At least one of the detector system, the disordered breathing detection system, the therapy control module, and the therapy delivery system includes an implantable component.

A further embodiment of the invention involves a disordered breathing therapy system. The system includes means for detecting disordered breathing and means for adapting a cardiac electrical therapy to mitigate the disordered breathing. The system further includes means for delivering the adapted therapy to the patient. At least one of the means for detecting disordered breathing, means for adapting a therapy to mitigate the disordered breathing, and means for delivering the adapted therapy includes an implantable component.

Another embodiment of the invention involves a system for providing therapy for disordered breathing. The system includes means for detecting disordered breathing and means for delivering a cardiac electrical therapy to the patient to mitigate the disordered breathing. The system further includes means for evaluating the effectiveness of the therapy and means for adapting the therapy to enhance the effectiveness of the therapy. At least one of the means for detecting the disordered breathing, the means for delivering the disordered breathing, the means for evaluating the effectiveness of the disordered breathing, and the means for adapting the disordered breathing to enhance effectiveness includes an implantable component.

Yet another embodiment of the invention includes means for detecting disordered breathing in a patient and means for adapting a cardiac electrical therapy to mitigate the disordered breathing while adjusting an impact of the therapy on the patient. The adapted therapy is delivered to the patient. At least one of the means for detecting the disordered breathing, the means for adapting a therapy to mitigate the disordered breathing, and the means for delivering the adapted therapy to the patient includes an implantable component.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
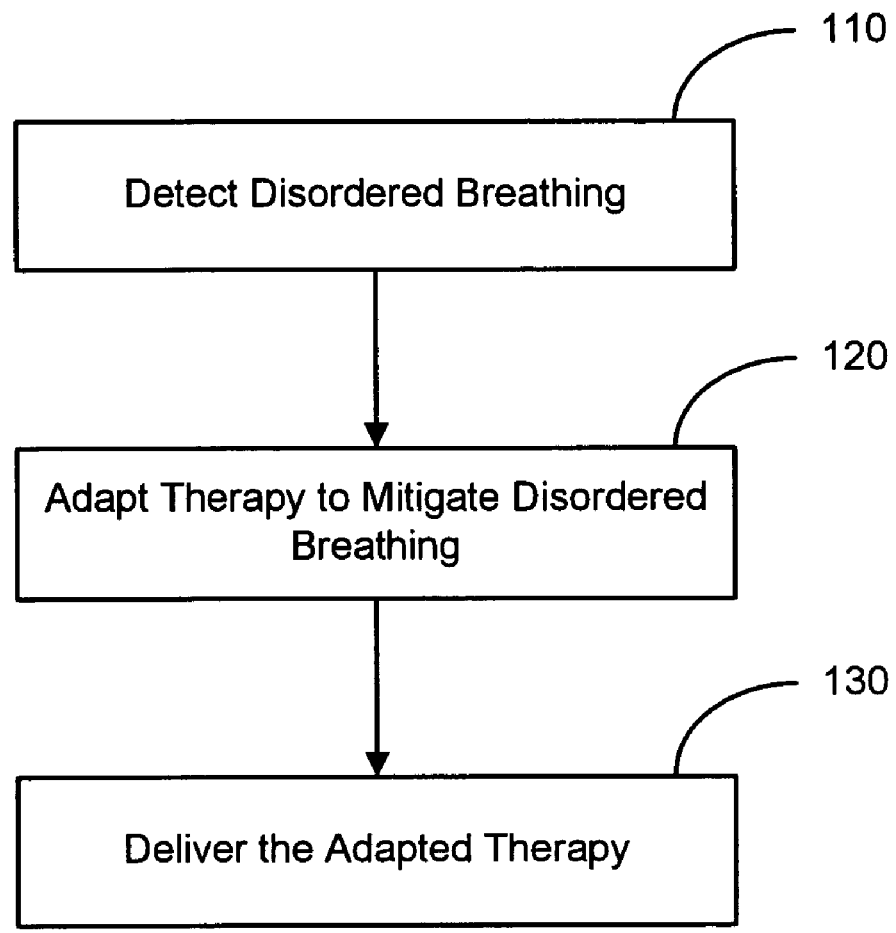
FIGS. 1-3 are a flow graphs illustrating methods for providing disordered breathing therapy in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

A significant percentage of patients between the ages of 30 and 60 experience some symptoms of disordered breathing. Disordered breathing primarily occurs during sleep, and is associated with excessive daytime sleepiness, systemic hypertension, increased risk of stroke, angina, and myocardial infarction. Disordered breathing is particularly prevalent among congestive heart failure patients, and may contribute to the progression of heart failure.

Various therapies have been used to treat disordered breathing, including both central and obstructive types. Obstructive sleep apnea has been associated with prolapse of the tongue and its surrounding structure into the pharynx, thus occluding the respiratory pathway. A commonly prescribed treatment for obstructive apnea is continuous positive airway pressure (CPAP). A CPAP device delivers air pressure through a nasal mask worn by the patient. The application of continuous positive airway pressure keeps the patient's throat open, reducing or eliminating the obstruction causing the apnea.

Prolapse of the tongue muscles has been attributed to diminishing neuromuscular activity of the upper airway. A treatment for obstructive sleep apnea involves compensating for the decreased muscle activity by electrical activation of the tongue muscles. The hypoglossal (HG) nerve innervates the protrusor and retractor tongue muscles. An appropriately applied electrical stimulation to the hypoglossal nerve, for example, may prevent backward movement of the tongue, thus preventing the tongue from obstructing the airway.

Cardiac pacing during periods of sleep or wakefulness may reduce incidents of disordered breathing. Various embodiments discussed herein relate to systems and methods for adapting an effective cardiac electrical therapy to mitigate disordered breathing. Such a therapy may be adapted, for example, to achieve an overall level of therapy efficacy. The therapy may be adapted to provide a tiered therapy capable of achieving a variety of therapeutic goals. For example, the therapy may be adapted to prevent further disordered breathing episodes, to terminate a detected disordered breathing episode, and/or to achieve a desired reduction in the overall frequency and/or severity of disordered breathing episodes. The cardiac electrical therapy may also be adapted to provide a therapy that balances therapeutic goals with conservation of device life, for example.

The therapy may be adapted to adjust the impact of the therapy on the patient, for example, to reduce the impact of the therapy on the patient. In adapting a reduced impact therapy, the system may take into account various conditions for evaluating the impact of the therapy on the patient. For example, conditions such as patient comfort, as indicated by patient feedback, undesirable side effects, stress on physiological systems involved in the disordered breathing therapy, interaction with cardiac pacing algorithms, e.g., bradycardia pacing, cardiac resynchronization pacing and/or anti-tachycardia pacing, as determined by interactive effects of the disordered breathing therapy with cardiac pacing, and/or sleep quality, as measured by one or more sleep quality indices, may be taken into account to adapt a therapy that reduces an impact of the therapy on the patient.

In addition, impact to the patient may involve a decreased useful service life of an implantable therapeutic device used to deliver disordered breathing therapy and/or pacing therapy for cardiac dysfunction. For example, a level of disordered breathing therapy may be unacceptably high if the energy requirements of the therapy result in an excessively decreased device service life. In this situation, early device removal and replacement produces a negative impact to the patient. Therefore, cardiac electrical therapy to mitigate disordered breathing may be adapted based on a projected decrease in device lifetime.

In one implementation, therapy approaches described herein may be used within the structure of an advanced patient management system. In this implementation, an advanced patient management system having capability for adaptive disordered breathing therapy allows a physician to remotely and automatically monitor cardiac and/or respiratory functions, as well as other patient conditions, and to initiate or modify therapy, if desired. In one example, an implantable cardiac rhythm management system, such as a cardiac pacemaker, defibrillator, or resynchronization device, or other device may be equipped with various telecommunications and information technologies to enable real-time data collection, diagnosis, and treatment of the patient. Systems and methods involving advanced patient management techniques are described in U.S. Pat. Nos. 6,336,903, 6,312,378, 6,270,457, and 6,398,728 which are incorporated herein by reference in their respective entireties.

The flowchart of FIG. 1 illustrates a method for providing cardiac electrical therapy to mitigate disordered breathing in accordance with embodiments of the invention. The method includes detecting disordered breathing 110 in the patient. Disordered breathing may be detected by analyzing one or more patient conditions indicative of disordered breathing. Table 1 provides a representative set of conditions that may be used in connection with disordered breathing detection. The use of other conditions or additional conditions to detect disordered breathing is also possible.

If disordered breathing is detected, a cardiac electrical therapy is adapted 120 to mitigate the disordered breathing. The therapy may be adapted, for example, to achieve a desired therapeutic goal, to reduce the impact of the therapy, and/or to balance therapy efficacy with therapy impact. Therapy impact involves situations that may result in patient stress, patient discomfort, reduction in sleep quality, interactions with other pacing algorithms, and/or decrease in the life of the therapy device. The adapted therapy is delivered 130 to the patient.

Once initiated, the system may continue to detect patient conditions and therapy may be modified based on periodically updated assessments of therapy efficacy, patient comfort during therapy, sleep quality during therapy, pacing interactions, or other factors, for example. At least one of the processes involved in detecting disordered breathing, adapting the therapy to mitigate the disordered breathing, and delivering the therapy is performed at least in part implantably. Implantably performing an operation comprises performing the operation using a component, device, or system that is partially or fully implanted within the body.

Patient conditions used to detect disordered breathing and adapt therapy to mitigate the disordered breathing may include both physiological and non-physiological conditions. The physiological conditions may include a broad category of conditions associated with the internal physiological conditions of the patient. Physiological conditions may be further subdivided, for example, into conditions of the cardiovascular, respiratory, and nervous systems, blood chemistry, body-related, e.g., posture and activity, in addition to respiration quality, sleep quality, and comfort as reported by the patient.

Contextual conditions generally encompass non-physiological patient-external or background conditions. Contextual conditions may be broadly defined to include, for example, present environmental conditions such as patient location, ambient temperature, humidity, air pollution index, as well as historical/background conditions relating to the patient, including the patient's normal sleep time and the patient's medical history, for example. Methods and systems for detecting some contextual conditions, including, for example, proximity to bed detection, are described in commonly owned U.S. Pat. No. 7,400,928, which is incorporated by reference herein in its entirety.

Table 1 provides a representative set of patient conditions that may be used to detect disordered breathing and/or adapt therapy to mitigate the disordered breathing. Table 1 also provides example sensing methods that may be employed to sense the conditions.

TABLE 1

| Condition Category | | | Condition used to detect disordered breathing and/or adapt therapy | Sensing method examples |
|---|---|---|---|---|
| Physiological | Sleep and Respiration Quality/ Patient Comfort | Sleep Fragmentation (arousal-based measures) | Sleep efficiency<br>Arousals/hour<br>Undisturbed sleep time<br>Undisturbed sleep efficiency<br>Sleep disturbance index<br>Undisturbed sleep time<br>Sleep staging | Electroencephlogram (EEG)<br>Electromyogram (EMG)<br>Activity sensor (accelerometer,<br>Transthoracic impedance sensor)<br>Posture sensor<br>Sleep stage detector (muscle atonia sensor) |
| | | Disturbed Breathing-Based Measures | Percent time in periodic breathing<br>Apnea/hypopnea index | Transthoracic impedance sensor |
| | | Patient-reported | Restful sleep<br>Patient comfort | Patient log |
| | Cardiovascular System | | Heart rate<br>Heart rate variability (HRV)<br>Ventricular filling pressure<br>Blood pressure | EGM<br>Electrocardiogram (ECG)<br>Intracardiac pressure sensor<br>Blood pressure sensor |
| | Respiratory System | | Snoring<br><br>Respiration pattern<br>(Tidal volume Minute ventilation Respiratory rate)<br>Patency of upper airway | Accelerometer<br>Microphone<br>Transthoracic pressure sensor (AC)<br><br>Intrathoracic impedance |

TABLE 1-continued

| Condition Category | | Condition used to detect disordered breathing and/or adapt therapy | Sensing method examples |
|---|---|---|---|
| | | Pulmonary congestion | sensor<br>Transthoracic impedance sensor (DC) |
| | Nervous System | Sympathetic nerve activity | Muscle sympathetic nerve Activity sensor<br>HRV via EGM or ECG |
| | Blood Chemistry | CO2 saturation | CO2 sensor |
| | | O2 saturation | O2 sensor |
| | | Blood alcohol content | Breathalyzer |
| | | Adrenalin | Blood analysis |
| | | Brain Natriuretic Peptide (BNP) | Blood analysis |
| | | C-Reactive Protein | Blood analysis |
| | | Drug/Medication/Tobacco use | Patient-reported |
| | Body-Related | Posture | Posture sensor |
| | | Activity | Accelerometer, MV, etc. |
| Contextual | Environmental | Ambient Temperature | Thermometer |
| | | Humidity | Hygrometer |
| | | Location | GPS, proximity sensor |
| | | Pollution | Air quality website |
| | | Time | Clock |
| | | Ambient light | Photodetector |
| | | Noise | Microphone |
| | | Barometric Pressure | Barometer |
| | | Altitude | Altimeter |
| | Historical/Background | Historical sleep time | Historical sensor data |
| | | History of disordered breathing | Patient log |
| | | Medical/psychological history | Medical records |

A subset of patient conditions, for example, one or more of the representative conditions listed in Table 1, may be used in connection with the detection of disordered breathing. Another subset, which may include conditions also used for disordered breathing detection, may be used in connection with therapy assessment and adaptation.

Detection of disordered breathing may involve detecting one or more conditions indicative of disordered breathing. According to one implementation, disordered breathing may be detected by monitoring the respiratory waveform output of a transthoracic impedance sensor to detect the patients' respiration tidal volume. When the patient's tidal volume falls below a predetermined threshold, a disordered breathing episode may be declared.

Another implementation of disordered breathing detection, discussed in more detail below, involves detection and analysis of respiratory waveform patterns. Methods and systems for detecting disordered breathing based on respiration patterns are more fully described in commonly owned U.S. Pat. No. 7,252,640, which is incorporated herein by reference in its entirety.

Disordered breathing detection may further involve classifying or otherwise identifying the detected disordered breathing episodes. For example, a patient may have a history of sleep-disordered breathing and the patient's therapy may be directed to mitigating disordered breathing episodes detected during sleep. In this situation, the disordered breathing therapy system may confirm that the patient is asleep before delivering the therapy. A method of sleep detection is described in commonly owned U.S. Pat. No. 7,189,204, which is incorporated herein by reference in its entirety.

Classification of sleep state, including classification of rapid eye movement sleep (REM sleep) and non-REM sleep may also be used to enhance sleep detection and/or to determine the duration of various sleep states. The most restful sleep occurs during non-REM sleep states. It may be beneficial to have information regarding the duration of various sleep states to determine the impact of therapy on the quality of sleep experienced by the patient during therapy delivery. Methods and systems involving classifying the patient's sleep state are described in commonly owned U.S. Publication No. 2005/0043652, filed concurrently with this application and incorporated herein by reference.

In another implementation, the disordered breathing therapy system may classify disordered breathing episodes with respect to a severity or type of disordered breathing, e.g., apnea, hypopnea, or mixture of apnea and hypopnea, so that an appropriate therapy can be adapted.

The patient conditions listed in Table 1 may be used in a multi-sensor approach to detect and confirm episodes of disordered breathing. For example, the accuracy of a preliminary disordered breathing detection may be enhanced by verifying the patient is asleep, in bed, inactive, lying down, or that the present environmental conditions are associated with disordered breathing in the patient.

Table 2 provides examples of how a representative subset of the physiological and contextual conditions listed in Table 1 may be used in connection with disordered breathing detection.

TABLE 2

| Condition Type | Condition | Examples of how condition may be used in disordered breathing detection |
|---|---|---|
| Physiological | Heart rate | Decrease in heart rate may indicate disordered breathing episode. |
| | | Decrease in heart rate may indicate the patient is asleep. |
| | Heart rate variability | Disordered breathing causes heart rate variability to decrease. Changes in HRV associated with sleep disordered breathing may be observed while the patient is awake or asleep |
| | Ventricular filling pressure | May be used to identify/predict pulmonary congestion associated with respiratory disturbance. |
| | Blood pressure | Swings in on-line blood pressure measures are associated with apnea. Disordered breathing generally increases blood pressure variability - these changes may be observed while the patient is awake or asleep. |
| | Snoring | Snoring is associated with a higher incidence of obstructive sleep apnea and may be used to detect disordered breathing. |
| | Respiration pattern/rate | Respiration patterns including, e.g., respiration rate, may be used to detect disordered breathing episodes. |
| | | Respiration patterns may be used to determine the type of disordered breathing. |
| | | Respiration patterns may be used to detect that the patient is asleep. |
| | Patency of upper airway | Patency of upper airway is related to obstructive sleep apnea and may be used to detect episodes of obstructive sleep apnea. |
| | Pulmonary congestion | Pulmonary congestion is associated with respiratory disturbances. |
| | Sympathetic nerve activity | End of apnea associated with a spike in SNA. Changes in SNA observed while the patient is awake or asleep may be associated with sleep disordered breathing |
| | CO2 | Low CO2 levels initiate central apnea. |
| | O2 | O2 desaturation occurs during severe apnea/hypopnea episodes. |
| | Blood alcohol content | Alcohol tends to increase incidence of snoring & obstructive apnea. |
| | Adrenalin | End of apnea associated with a spike in blood adrenaline. |
| | BNP | A marker of heart failure status, which is associated with Cheyne-Stokes Respiration |
| | C-Reactive Protein | A measure of inflammation that may be related to apnea. |
| | Drug/Medication/Tobacco use | These substances may affect the incidence of both central & obstructive apnea. |
| | Muscle atonia | Muscle atonia may be used to detect REM and non-REM sleep. |
| | Eye movement | Eye movement may be used to detect REM and non-REM sleep. |
| Contextual | Temperature | Ambient temperature may be a condition predisposing the patient to episodes of disordered breathing and may be useful in disordered breathing detection. |
| | Humidity | Humidity may be a condition predisposing the patient to episodes of disordered breathing and may be useful in disordered breathing detection. |
| | Pollution | Pollution may be a condition predisposing the patient to episodes of disordered breathing and may be useful in disordered breathing detection. |
| | Posture | Posture may be used to confirm or determine the patient is asleep. |
| | Activity | Patient activity may be used in relation to sleep detection. |
| | Location | Patient location may used to determine if the patient is in bed as a part of sleep detection. |

Episodes of disordered breathing are associated with acute and chronic physiological effects. Acute responses to disordered breathing may include, for example, negative intrathoracic pressure, hypoxia, arousal from sleep, and increases in blood pressure and heart rate. During obstructive apnea episodes, negative intrathoracic pressure may arise from an increased effort to generate airflow. Attempted inspiration in the presence of an occluded airway results in an abrupt reduction in intrathoracic pressure. The repeated futile inspiratory efforts associated with obstructive sleep apnea may trigger a series of secondary responses, including mechanical, hemodynamic, chemical, neural, and inflammatory responses.

Obstructive sleep apneas may be terminated by arousal from sleep several seconds after the apneic peak, allowing the resumption of airflow. Coincident with arousal from sleep, surges in sympathetic nerve activity, blood pressure, and heart rate may occur. The adverse effects of obstructive apnea are not confined to sleep. Daytime sympathetic nerve activity and systemic blood pressure are increased. There may also be a sustained reduction in vagal tone, causing reduction in total heart rate variability during periods of wakefulness.

Central sleep apnea is generally caused by a failure of respiratory control signals from the brain. Central sleep apnea is a component of Cheyne-Stokes respiration (CSR), a respiration pattern primarily observed in patients suffering from chronic heart failure (CHF). Cheyne-Stokes respiration is a form of periodic breathing in which central apneas and hypopneas alternate with periods of hyperventilation causing a waxing-waning pattern of tidal volume. In some CHF patients, obstructive sleep apnea and central sleep apnea may coexist. In these patients, there may be a gradual shift from predominantly obstructive apneas at the beginning of the night to predominantly central apneas at the end of the night.

Several mechanisms may be involved in central apneas observed in patients suffering from chronic heart failure. According to one mechanism, increased carbon dioxide sensitivity in CHF patients triggers hyperventilation initiating a sleep apnea episode. Breathing is regulated by a negative feedback system that maintains the arterial partial pressure of carbon dioxide ($PaCO_2$) within limits. Changes in $PaCO_2$ lead to changes in ventilation wherein the greater the sensitivity to carbon dioxide, the greater the ventilatory response.

In patients with cardiopulmonary disorders, an increase in carbon dioxide sensitivity may minimize perturbations in $PaCO_2$, thus protecting them against the long-term consequences of hypercapnia, an excess of carbon dioxide in the blood. This protective mechanism may be advantageous while the patient is awake, however, the increased sensitivity to carbon dioxide may disrupt breathing during sleep.

During sleep, ventilation decreases and $PaCO_2$ levels increase. If the $PaCO_2$ level decreases below level referred to as the apneic threshold, ventilation ceases, central sleep apnea ensues, and $PaCO_2$ rises to previous levels.

In patients with increased sensitivity to carbon dioxide, the negative-feedback system that controls breathing initiates a large ventilatory response when $PaCO_2$ rises. The resultant hyperventilation, by driving the $PaCO_2$ level below the apneic threshold, results in central sleep apnea. As a result of the apnea, the $PaCO_2$ level rises again, leading to an increase in ventilation. In this way, cycles of hyperventilation and central apnea may recur throughout sleep.

The posture of CHF patients during sleep may also be implicated in triggering apnea. When CHF patients lie down the prone posture may create central fluid accumulation and pulmonary congestion causing the patient to reflexively hyperventilate, that may lead to the cyclical pattern of hyperventilation-apnea described above.

Arousals are not necessarily required in central sleep apneas for the resumption of breathing at the termination of the apneic event. In central apnea, the arousals follow the initiation of breathing and may facilitate the development of oscillations in ventilation by recurrently stimulating hyperventilation and reducing $PaCO_2$ below the apneic threshold. Once triggered, the pattern of alternating hyperventilation and apnea is sustained by the combination of increased respiratory drive, pulmonary congestion, arousals, and apnea-induced hypoxia causing $PaCO_2$ oscillations above and below the apneic threshold. Shifts in the patient's state of consciousness, particularly with repeated arousals, may further destabilize breathing.

With the transition from wakefulness to NREM sleep, the waking neural drive to breathe is lost, and the threshold for a ventilatory response to carbon dioxide is increased. Therefore, if the patient's $PaCO_2$ level during wakefulness is below this higher sleeping threshold, the transition to NREM sleep may be accompanied by a transient loss of respiratory drive resulting in a central apnea. During the apnea, the $PaCO_2$ rises until it reaches the new higher threshold level and initiates breathing. If sleep becomes firmly established, regular breathing resumes. However, if an arousal should occur, the increased $PaCO_2$ level associated with sleep is now relatively too high for a state of wakefulness and will stimulate hyperventilation. Thus, although arousals terminate obstructive sleep apneas, arousals trigger the respiratory oscillations associated with central apneas, particularly Cheyne-Stokes respiration.

In addition to the acute responses to sleep disordered breathing, such as those discussed above, sleep disordered breathing is also associated with a number of secondary or chronic responses, including, for example, chronic decrease in heart rate variability (HRV) and blood pressure changes. Patients with central sleep apnea may have higher urinary and circulating norepinephrine concentrations and lower $PaCO_2$ during both sleep and wakefulness.

Acute responses to disordered breathing may be used to detect disordered breathing and both acute and chronic responses may be used to assess the efficacy and impact of disordered breathing therapy. In one implementation, a first subset of patient conditions may be used to detect disordered breathing. A second subset of patient conditions, possibly overlapping the subset used for disordered breathing detection, may be used to assess the disordered breathing therapy for adapting the disordered breathing therapy. For example, according to one embodiment, the therapy may be adapted to enhance the efficacy of the therapy. In another embodiment, the therapy may be adapted to reduce an impact of the therapy on the patient. In yet a further embodiment, the therapy may be adapted both to enhance therapy effectiveness and to reduce an impact of the therapy on the patient.

Conditions used to assess therapy effectiveness may be different from, or the same as, conditions used to assess an impact of the therapy on the patient. Table 3 provides a representative set of conditions that may be used for therapy assessment.

TABLE 3

| Condition | Therapy Impact | Therapy Efficacy |
|---|---|---|
| Arousal-Based Sleep Fragmentation Measures | May be used to assess therapy impact during sleep. | |
| Restful sleep (Patient reported) | May be used to assess therapy impact during sleep. | |
| Discomfort (Patient reported) | May be used to assess therapy impact. | |
| Pacing algorithm interaction | May be used to assess therapy impact. | |
| Remaining useful life of therapy device | May be used to assess therapy impact. | |
| Disturbed Breathing-Based Measures | | May be used to analyze/assess efficacy of therapy to mitigate disordered breathing episodes. |
| Respiration quality (Patient reported) | | May be used to analyze/assess efficacy of therapy to mitigate disordered breathing episodes. |

TABLE 3-continued

| Condition | Therapy Impact | Therapy Efficacy |
|---|---|---|
| Heart rate variability (HRV) | | Disordered breathing causes heart rate variability to decrease. Therapy may be modified based on changes in HRV |
| Blood pressure | | Disordered breathing causes blood pressure increase |
| Sympathetic nerve activity (SNA) | | Changes in sympathetic nerve activity are caused by disordered breathing. Therapy may be adjusted based on the level of SNA |
| Blood chemistry | | A number of disordered breathing related changes may occur in a patient's blood chemistry, including, e.g., higher norepinephrine levels, and lower $PaCO_2$ |

It is understood that the patient conditions that may be used in connection with disordered breathing therapy, including detection of disordered breathing and/or therapy assessment, for example, are not limited to the representative sets listed in Tables 1-3 or those described herein. Further, although illustrative sensing methods for detecting the patient conditions listed above are provided, it is understood that the patient conditions may be detected using a wide variety of technologies. The embodiments and features described in herein are not limited to the particular patient conditions or the particular sensing technologies provided.

In accordance with various embodiments of the invention, conditions related to sleep quality, e.g., sleep fragmentation and/or other arousal-based measures, patient-reported restful sleep, and patient-reported discomfort during therapy, may be used to assess the impact of the therapy on the patient. For example, if a patient is receiving effective disordered breathing therapy and has low sleep fragmentation, reports restful sleep, and reports no discomfort, the adverse effects of the therapy on the patient may be relatively low. If sleep fragmentation is relatively high, or if the patient reports discomfort or feeling tired after sleeping, these conditions may indicate that therapy is causing sleep disturbances and/or other undesirable effects.

Because disordered breathing generally occurs during sleep, it may be particularly important to assess sleep quality during disordered breathing therapy delivery. It is undesirable to provide therapy that eliminates the disordered breathing but increases sleep fragmentation. In such a situation, the disordered breathing therapy may exacerbate the adverse effects produced by the respiratory disturbances. Thus, it may be preferable to assess the impact of the therapy on the patient and adjust the therapy to improve sleep quality. Various methods and systems for collecting sleep quality data and evaluating sleep quality are described in a commonly owned U.S. Publication No. 2005/0042589, filed concurrently with this application which is hereby incorporated herein by reference in its entirety.

Sleep fragmentation and sleep disruptions may also occur if disordered breathing therapy is ineffective and disordered breathing occurs during sleep. Therefore, a therapy impact assessment based on detected sleep quality and/or patient-reported restful sleep may preferably take into account an assessment of therapy effectiveness.

Some patients may receive cardiac electrical stimulation therapy for both disordered breathing as well as cardiac disorders such as bradycardia and/or CHF. Interactions may occur between cardiac electrical therapy to mitigate disordered breathing and the patient's cardiac pacing regimen, e.g., pacing for bradycardia or cardiac resynchronization. Such interactions may be factored into the assessment of the impact of disordered breathing therapy on the overall therapy delivered to the patient.

Interactions between cardiac therapy and disordered breathing therapy may occur, and detection of the interactions may be used to adjust therapy. In some cases, cardiac electrical therapy to mitigate disordered breathing may enhance cardiac pacing therapy directed to alleviate a cardiac dysfunction, such as bradycardia or CHF. For example, non-excitatory electrical stimulation of the left ventricle during an absolute refractory period may be beneficial to treat both CHF and disordered breathing.

In other examples, cardiac electrical therapy for disordered breathing may work at cross purposes with the patient's cardiac pacing regimen. A pacing therapy delivered for treatment of disordered breathing may increase the percentage of heart beats initiated by atrial pacing. However, a concurrent cardiac resynchronization therapy may be optimal when intrinsic atrial events are allowed to initiate a heart beat. In this situation, the disordered breathing therapy, the cardiac resynchronization therapy, or both therapies, may be adjusted to reduce undesirable therapy interactions.

Evaluation of the impact of disordered breathing therapy on the patient preferably takes into consideration the impact of disordered breathing therapy on the overall therapeutic goals for the patient, including cardiac pacing goals and disordered breathing goals. The disordered breathing therapy may involve a variety of therapy regimens implemented to achieve predetermined therapeutic goals. The effectiveness of the therapy, or the degree to which the therapy meets one or more therapeutic goals may be assessed by detecting and analyzing episodes of disordered breathing that occur during therapy delivery.

For example, a therapeutic goal may involve terminating a disordered breathing episode and the disordered breathing therapy may be adapted to achieve this goal. Additionally, or alternatively, a therapeutic goal may involve terminating a disordered breathing episode and preventing further disordered breathing. In this example situation, the therapy regimen may be adapted to provide a first therapy to terminate the disordered breathing episode and provide a second preventative therapy to reduce or eliminate further disordered breathing episodes. The second preventative therapy may be adapted to reduce episodes of disordered breathing below a predetermined disordered breathing episode threshold. A disordered breathing episode threshold may be expressed, for example, in terms of an apnea/hypopnea index (AHI) or percent time in periodic breathing (% PB).

Figure 2:
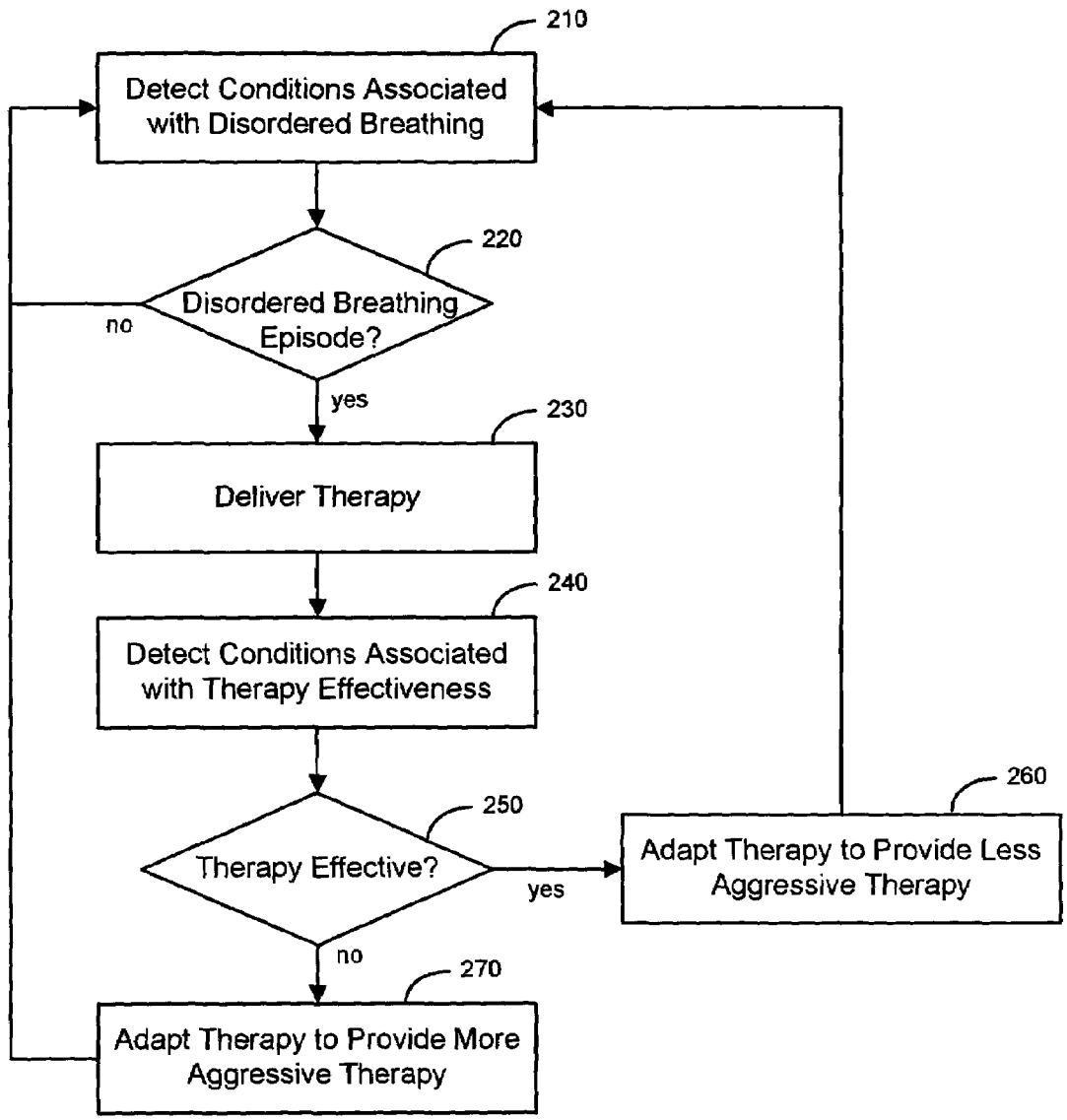
Figure 3:
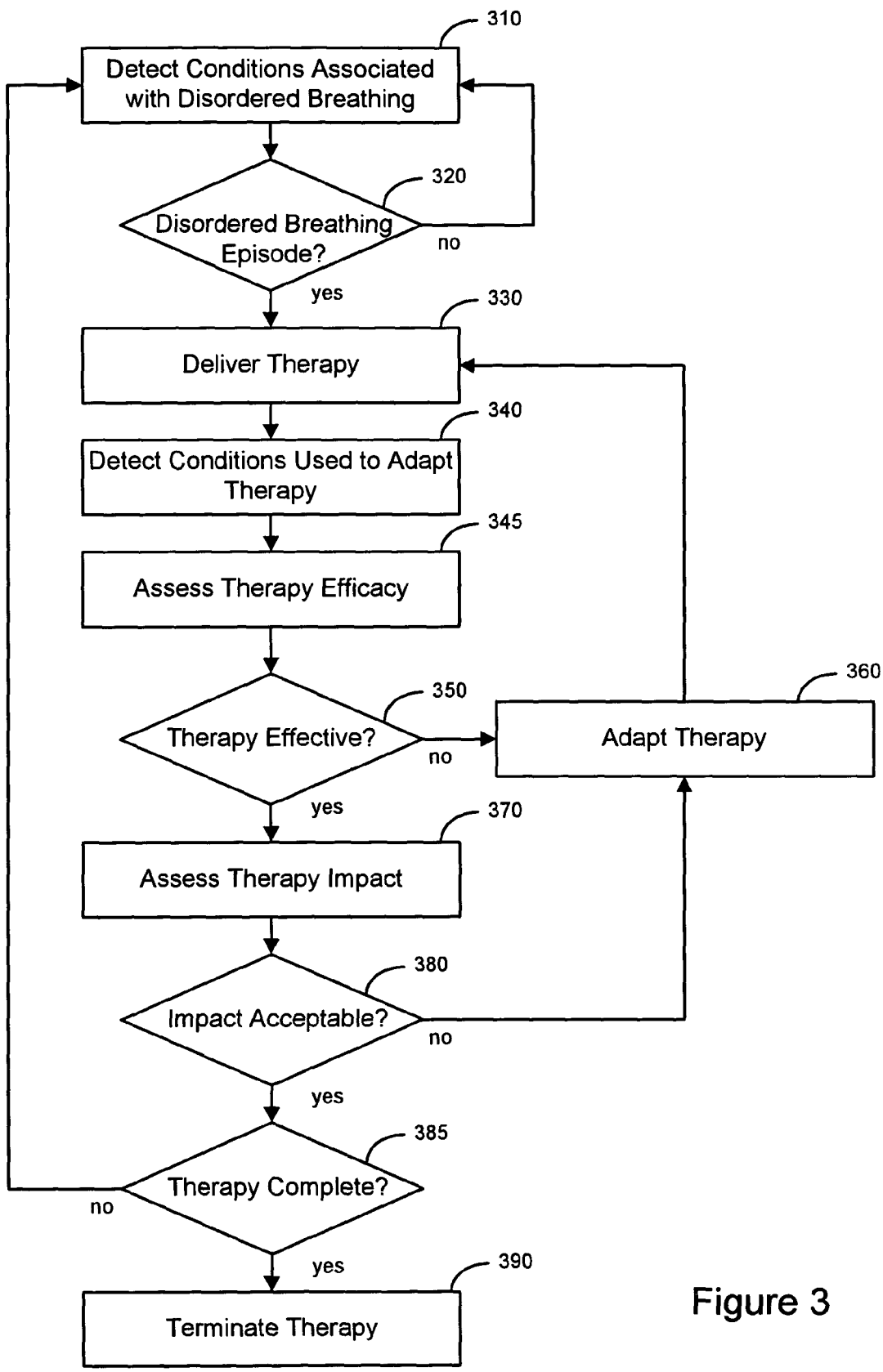

FIGS. 2 and 3 are flow graphs illustrating methods of adapting a disordered breathing therapy according to embodiments of the invention. The flow graph of FIG. 2 illustrates a method of adapting disordered breathing therapy to achieve a desired level of therapy efficacy. In this embodiment, a first set of conditions associated with disordered breathing is detected 210 and used to determine if a disordered breathing episode is occurring. If disordered breathing is detected 220, disordered breathing therapy is delivered 230 to the patient to mitigate the disordered breathing. In one embodiment, the therapy delivered to the patient may include, for example, cardiac pacing at a rate in excess of an intrinsic rate, or in excess of a normally programmed rate, such as a normally programmed sleep rate.

Adapting the cardiac electrical therapy may also involve modifying the electrical stimulation energy with or without an increase in the pacing rate. Increased stimulation energy has been shown to produce higher cardiac contractility, which may be particularly beneficial for patients suffering from chronic heart failure. Loss of cardiac contractility is thought to initiate and drive the progression of heart failure, a disorder that is intertwined with Cheyne-Stokes respiration.

Further, adapting a cardiac electrical therapy to mitigate disordered breathing may involve adapting a therapy involving non-excitatory electrical stimulation of one or more heart chambers, e.g., the left and/or right ventricles, or other cardiac sites. Non-excitatory electrical stimulation may be delivered during absolute refractory periods of the cardiac tissue, for example, to improve cardiac contractility. The non-excitatory stimulation therapy may be used alone or in combination with the pacing to provide a comprehensive therapy regimen for patients with CHF and disordered breathing such as Cheyne-Stokes respiration.

In other embodiments, adapting the cardiac electrical therapy to mitigate disordered breathing may involve initiating a particular pacing regimen or switching from one pacing mode to another pacing mode. In one example, the cardiac pacing regimen may be switched from a dual-chamber pacing mode to a bi-ventricular or other resynchronization mode. In other examples, the pacing mode may be switched to a pacing mode that promotes atrial pacing, or promotes consistent ventricular pacing. In yet another example, the cardiac electrical therapy may involve initiating multi-site electrical stimulation to the heart or changing from one electrical stimulation site to another. The pacing mode may be switched from single chamber to multiple chambers, or the reverse. For example, a bi-ventricular mode may be switched to a left ventricular mode only. Alternatively, a single chamber mode, e.g., LV or RV, may be switched to a bi-ventricular mode. Other therapy regimens, involving various pacing modes, pacing sites, or non-excitatory electrical stimulations, are possible in connection with providing cardiac electrical therapy for disordered breathing. The type of cardiac electrical therapy beneficial to a patient is highly patient specific and may be determined based on the responses of a particular patient.

A second set of conditions associated with therapy effectiveness is sensed 240 and used to assess the effectiveness of the therapy. The detected conditions used to assess the efficacy of the therapy and adapt the therapy to mitigate disordered breathing may represent one or more of the acute conditions associated with disordered breathing, e.g., detected episodes of interrupted breathing, hypoxia, arousals, negative intrathoracic pressure, blood pressure, and heart rate or blood pressure surges.

Additionally, or alternatively, the conditions used to assess therapy efficacy and adapt the cardiac electrical therapy may include one or more chronic conditions associated with disordered breathing, including, for example, decreased heart rate variability, increased blood pressure, chronic changes in sympathetic nerve activity, and changes in blood chemistry, such as increased levels of $PaCO_2$ and norepinephrine levels, among others.

In general, a therapeutic goal in the treatment of disordered breathing is to provide the least aggressive therapy that effectively mitigates, terminates or prevents the patient's disordered breathing or achieves a particular therapeutic goal associated with disordered breathing therapy. The disordered breathing therapy regimen may be enhanced by increasing the intensity or level of therapy to more effectively mitigate the disordered breathing. Alternatively, the disordered breathing therapy regimen may be enhanced by reducing the intensity or level of therapy while maintaining a desired decrease in the severity or frequency of disordered breathing episodes, thus reducing undesirable side effects from the therapy and extending the device lifetime.

If the therapy effectiveness is acceptable 250, e.g., terminates or reduces the patient's disordered breathing or meets some other desired goal, then the therapy may be adapted 260 to provide a less aggressive therapy, e.g., decreased pacing rate, decreased pacing energy, or altered pacing mode, as described above. If the therapy is not effective 250, then the therapy may be adapted 270 to enhance therapy efficacy by providing a more aggressive therapy, e.g., increased pacing rate, increased pacing energy, or pacing mode switch.

In one embodiment, therapy may be determined to be ineffective if disordered breathing continues unmitigated following therapy delivery. In this situation, the therapy may be adapted to provide a more aggressive therapy, for example, cardiac pacing at a higher rate. In another embodiment, if the disordered breathing decreases sufficiently in severity, or is otherwise sufficiently mitigated, the therapy may be enhanced by adapting the therapy to provide a less aggressive therapy, e.g., pacing at a lower rate or a decreased energy level. As previously discussed, a less aggressive therapy is preferable to reduce the risk of arousal, to avoid unnecessary stress on the patient's heart, and to prolong battery life, for example.

The flow graph of FIG. 3 illustrates a method of adapting a disordered breathing therapy in accordance with embodiments of the invention. In this example, a first set of conditions associated with disordered breathing is detected 310 and used to determine if a disordered breathing episode is occurring. If disordered breathing is detected 320, therapy is delivered 330 to the patient to mitigate the disordered breathing.

A second set of conditions is detected 340 and used to adapt the therapy. Based on the second set of sensed conditions, the therapy efficacy is assessed 345. If the therapy efficacy is not acceptable 350, then the therapy may be adapted 360 to enhance therapy efficacy. If the therapy efficacy is acceptable 350, then the impact of the therapy on the patient may be assessed 370.

If the therapy impact on the patient is acceptable 380, the system continues to deliver the therapy. When the therapy regimen is complete 385, then therapy is terminated 390.

If the therapy impact on the patient exceeds acceptable limits, the therapy impact is not acceptable 380, and the therapy may be adapted 360 to reduce the therapy impact.

The methods illustrated in the flow graphs of FIGS. 2 and 3 contemplate real-time monitoring of patient conditions allowing the therapy system to dynamically adjust the therapy regimen to accommodate the changing needs of the patient. In one configuration, the therapy may be adjusted during the period that therapy is delivered to the patient. In another configuration, the therapy may be adapted between disordered breathing episodes or from night-to-night based on assessment of the efficacy of therapy delivered in connection with one or more previously detected disordered breathing episodes.

Figure 4:
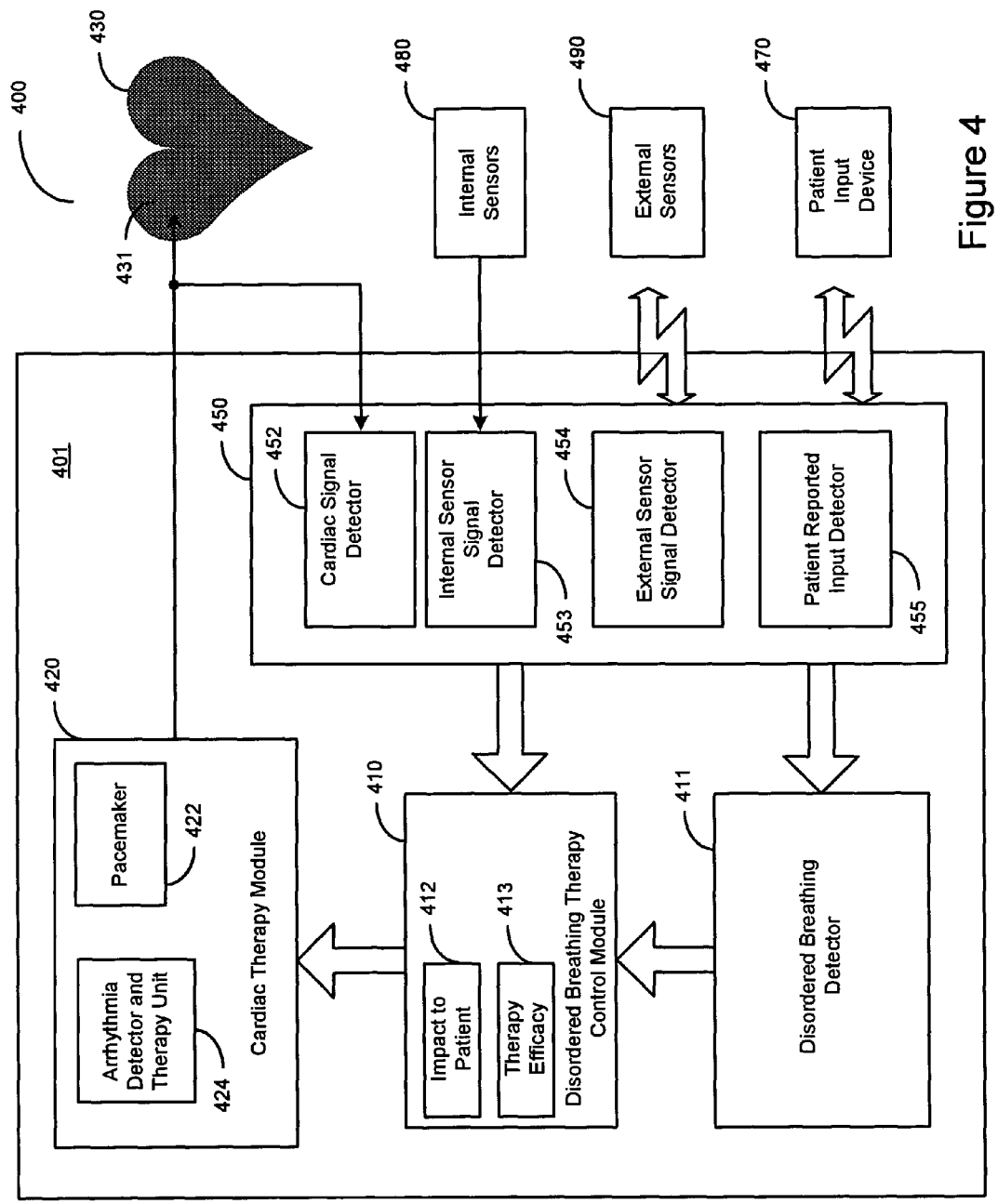
FIG. 4 is a block diagram of a medical device incorporating a disordered breathing therapy system in accordance with embodiments of the invention.

The block diagram of FIG. 4 illustrates a therapy system 400 that may be used to implement a disordered breathing therapy methodology in accordance with embodiments of the invention. FIG. 4 illustrates an implantable therapy control unit 401 that may be used to provide cardiac electrical therapy for delivering disordered breathing therapy as well as cardiac rhythm therapy. Various cardiac rhythm therapies, including dual chamber cardiac pacing, defibrillation, cardioversion, and/or cardiac resynchronization therapy, may be provided by the therapy system 400 separately or in coordination with disordered breathing therapy. Although illustrative embodiments involve therapy systems having an implantable therapy control system and implantable sensors, it is understood that a disordered breathing therapy system may be configured so that portions of the therapy control system are arranged externally to the patient. Further, the sensors and other components of the condition detector system may involve patient-external sensors or components, patient-internal sensors or components or a combination of patient-external and patient-internal sensors or other components.

Therapy control circuitry 401 may include circuitry for providing cardiac rhythm management, as well as disordered breathing therapy. The therapy control circuitry 401 may include, for example, a cardiac therapy module 420 including a pacemaker 422 and an arrhythmia detector/therapy unit 424. In this embodiment, the cardiac therapy module 420 is coupled to a lead system having implanted electrodes 431 to electrically couple the heart 430 to the therapy control circuitry 401.

Patient conditions may be detected using one or more patient-internal sensors 480, one or more patient-external sensors 490, and one or more patient input devices 470. One or more components of the therapy system 400 may be coupled using a wireless communications link. For example, some or all of the patient-internal sensors 480, patient-external sensors 490, and patient input devices 470 may use remote communication capabilities, such as a wireless proprietary or a wireless Bluetooth communications link or other proprietary wireless communications protocol. In one implementation, a wireless communications link couples the sensors 480, 490, input devices 470, and the associated detector circuitry 450 to other components of the therapy control circuitry.

The therapy control circuitry 401 includes detection circuitry 452, 453 for detecting physiological or contextual conditions using one or more patient-internal sensors 480, 431. In this example, signals from the implanted cardiac electrodes 431 are detected by the cardiac signal detector 452 and communicated to other therapy system components, including the cardiac therapy module 420, the disordered breathing detector 411, and the disordered breathing therapy control module 410. Additional patient-internal sensors 480 including, for example, one or more of the patient-internal sensors listed in Table 1, may also be utilized to detect patient conditions. The patient-internal sensors 480 may be coupled to the internal sensor signal detection circuitry 453 through conducting leads as shown, or through a wireless connection, for example.

In one implementation, the therapy control circuitry 401 may determine heart rate and tidal volume using cardiac and respiration signals derived from an intracardiac electrocardiogram (EGM) sensor and transthoracic impedance sensor, respectively. The electrocardiogram and transthoracic impedance sensors may be components of an implantable therapy system 400 that includes a cardiac pacemaker and/or defibrillator. The EGM and transthoracic impedance signals may be used in connection with cardiac rhythm management, as well as disordered breathing therapy. The therapy system 400 may derive additional physiological and non-physiological patient conditions using additional sensors and input devices. For example, a patient's activity may be detected using an implantable accelerometer, the patient's perceptions of restful sleep may be input using an external patient input device, and the patient's proximity to bed may be detected using a proximity to bed sensor involving both patient-internal and patient-external components.

The therapy control circuitry 401 may include external circuitry 454 for detecting sensor signals from external sensors. The therapy control circuitry 401 may further include patient-reported input circuitry 455 for detecting conditions reported by the patient or other person, e.g., patient perceptions of restful sleep or therapy comfort, through one or more patient input devices 470. Some or all of the components of the patient-external sensors 490, patient input devices 470, and the associated detection circuitry 454, 455 may be coupled to other components of the therapy system through a wireless link as discussed above.

The cardiac therapy module 420 receives cardiac signals from the implanted cardiac electrodes 431 and analyzes the cardiac signals to determine an appropriate therapy. The cardiac therapy may include pacing therapy controlled by the pacemaker 422 to treat cardiac rhythms that are too slow. In this situation, the pacemaker 422 controls the delivery of periodic low energy pacing pulses to one or more heart chambers to ensure that the periodic contractions of the heart are maintained at a hemodynamically sufficient rate.

The cardiac therapy may also include therapy to terminate tachyarrhythmia, wherein the heart rate is too fast. The arrhythmia detector/therapy unit 424 detects and treats episodes of tachyarrhythmia, including tachycardia and/or fibrillation. The arrhythmia detector/therapy unit 424 recognizes cardiac signals indicative of tachyarrhythmia and delivers high energy electrical stimulations to the heart 430 to terminate the arrhythmia.

The therapy control circuitry 401 includes a disordered breathing detector 411 coupled to the signal detection circuitry 450. The disordered breathing detector 411 receives signals representing one or more patient conditions associated with disordered breathing from the signal detection circuitry 450 and uses the patient conditions to detect and classify episodes of disordered breathing.

The disordered breathing detector 411 is coupled to the disordered breathing therapy control module 410. Therapy to mitigate disordered breathing may be initiated by the disordered breathing therapy control module 410 upon detection of disordered breathing. The disordered breathing therapy control module 410 adapts the disordered breathing therapy based on detected patient conditions associated with therapy efficacy or impact of the therapy on the patient.

As previously discussed, disordered breathing therapy may be adapted to achieve or maintain a predetermined therapeutic goal based on an assessment of therapy efficacy and/or impact on the patient. The disordered breathing therapy control module 410 may include, for example, circuitry for evaluating therapy efficacy 413 and therapy impact on the patient 412. In the embodiment illustrated in FIG. 4, the disordered breathing therapy control module 410 is coupled to the cardiac therapy module 420. The disordered breathing therapy module 410 cooperates with the cardiac therapy module 420 to control cardiac electrical therapy for disordered breathing delivered by the cardiac therapy module 420.

The cardiac therapy module 420, in cooperation with the disordered breathing therapy control module 410, delivers an appropriate cardiac electrical therapy to mitigate the disordered breathing. In various illustrative therapy regimens, pacing to mitigate disordered breathing may involve pacing at a rate exceeding an intrinsic rate, pacing at a rate above the patient's normal rate, or above the patient's normal sleep rate, pacing according to selected modes, e.g., bi-ventricular or single chamber modes, or pacing at a predetermined energy level. The pacing may involve any or all of the heart chambers, for example, right and left atria and right and left ventricles, and may further involve multi-site pacing within one heart chamber. In one example, the pacing pulses may be delivered to left and right ventricles substantially simultaneously, or according to other timing sequences.

According to various embodiments of the invention, detection of disordered breathing may be used to initiate an adaptable therapy to mitigate the disordered breathing. Disordered breathing detected during therapy delivery may be used to assess the effectiveness of the disordered breathing therapy. In various implementations, episodes of disordered breathing may be detected and classified by analyzing the patient's respiration patterns.

Figure 5:
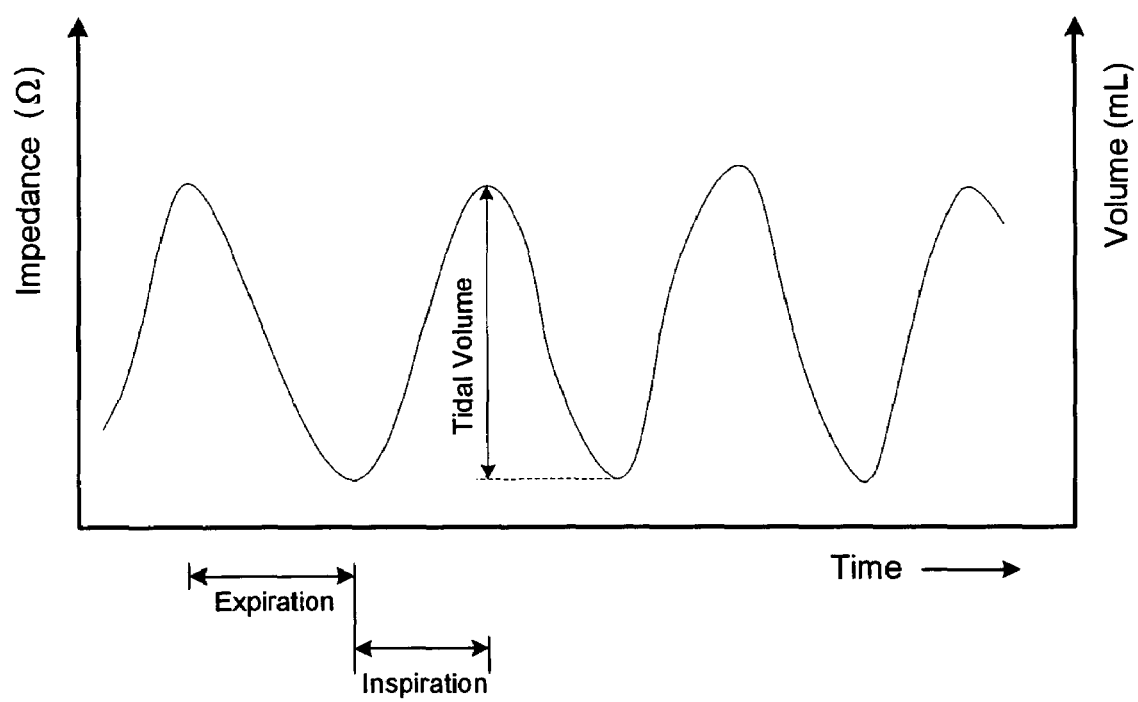
FIG. 5 illustrates a normal respiration pattern as represented by a transthoracic impedance sensor signal.

FIG. 5 illustrates normal respiration as represented by a signal produced by a transthoracic impedance sensor. The transthoracic impedance increases during respiratory inspiration and decreases during respiratory expiration. During non-REM sleep, a normal respiration pattern includes regular, rhythmic inspiration—expiration cycles without substantial interruptions.

In one embodiment, episodes of disordered breathing may be detected by monitoring the respiratory waveform output of the transthoracic impedance sensor. When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Figure 6:
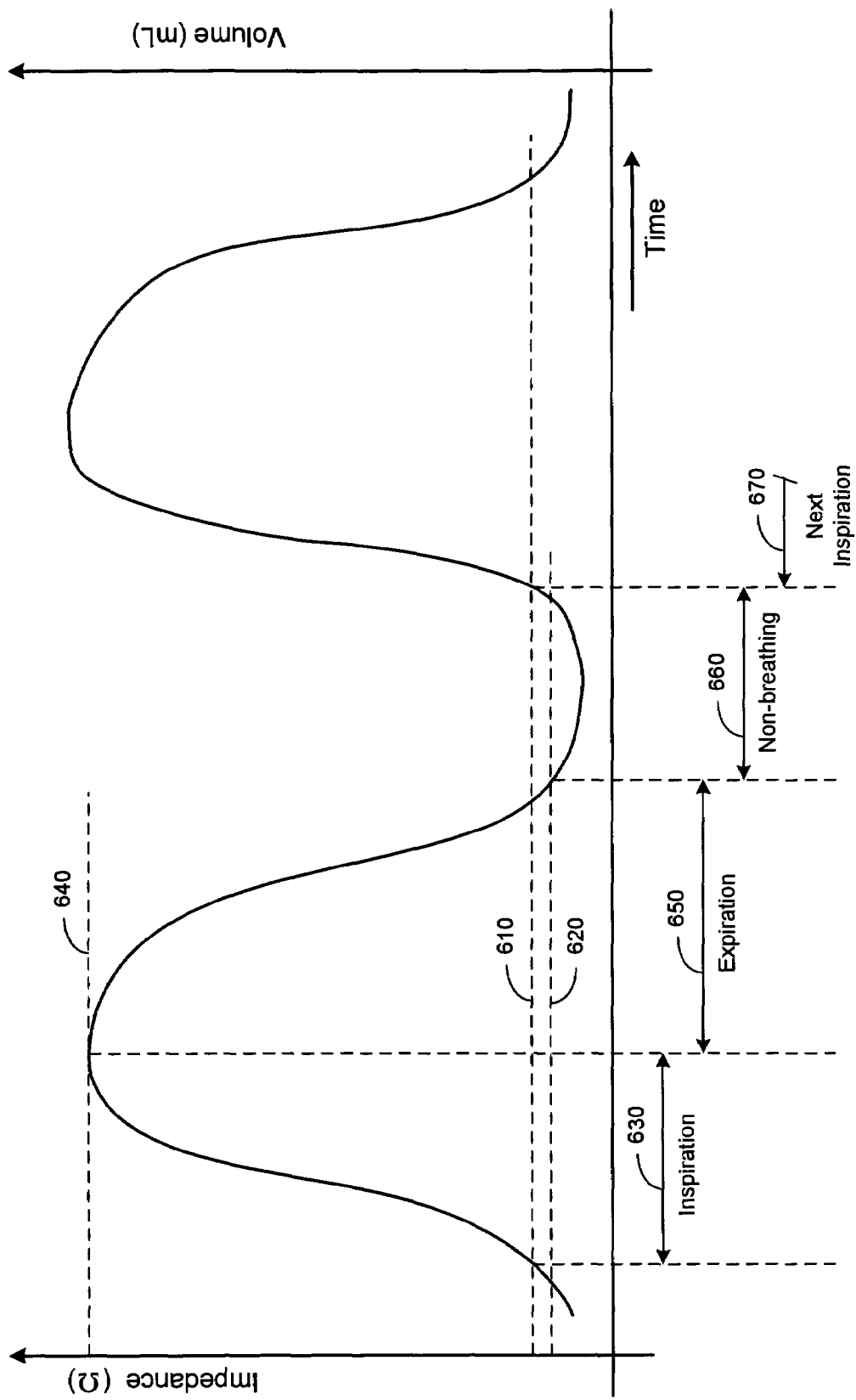
FIG. 6 illustrates respiration intervals used for disordered breathing detection according to embodiments of the invention.

In another embodiment, detection of disordered breathing involves defining and examining a number of respiratory cycle intervals. FIG. 6 illustrates respiration intervals used for disordered breathing detection according to an embodiment of the invention. A respiration cycle is divided into an inspiration period corresponding to the patient inhaling, an expiration period, corresponding to the patient exhaling, and a non-breathing period occurring between inhaling and exhaling. Respiration intervals are established using inspiration 610 and expiration 620 thresholds. The inspiration threshold 610 marks the beginning of an inspiration period 630 and is determined by the transthoracic impedance signal rising above the inspiration threshold 610. The inspiration period 630 ends when the transthoracic impedance signal is maximum 640. A maximum transthoracic impedance signal 640 corresponds to both the end of the inspiration interval 630 and the beginning of the expiration interval 650. The expiration interval 650 continues until the transthoracic impedance falls below an expiration threshold 620. A non-breathing interval 660 starts from the end of the expiration period 650 and continues until the beginning of the next inspiration period 670.

Figure 7:
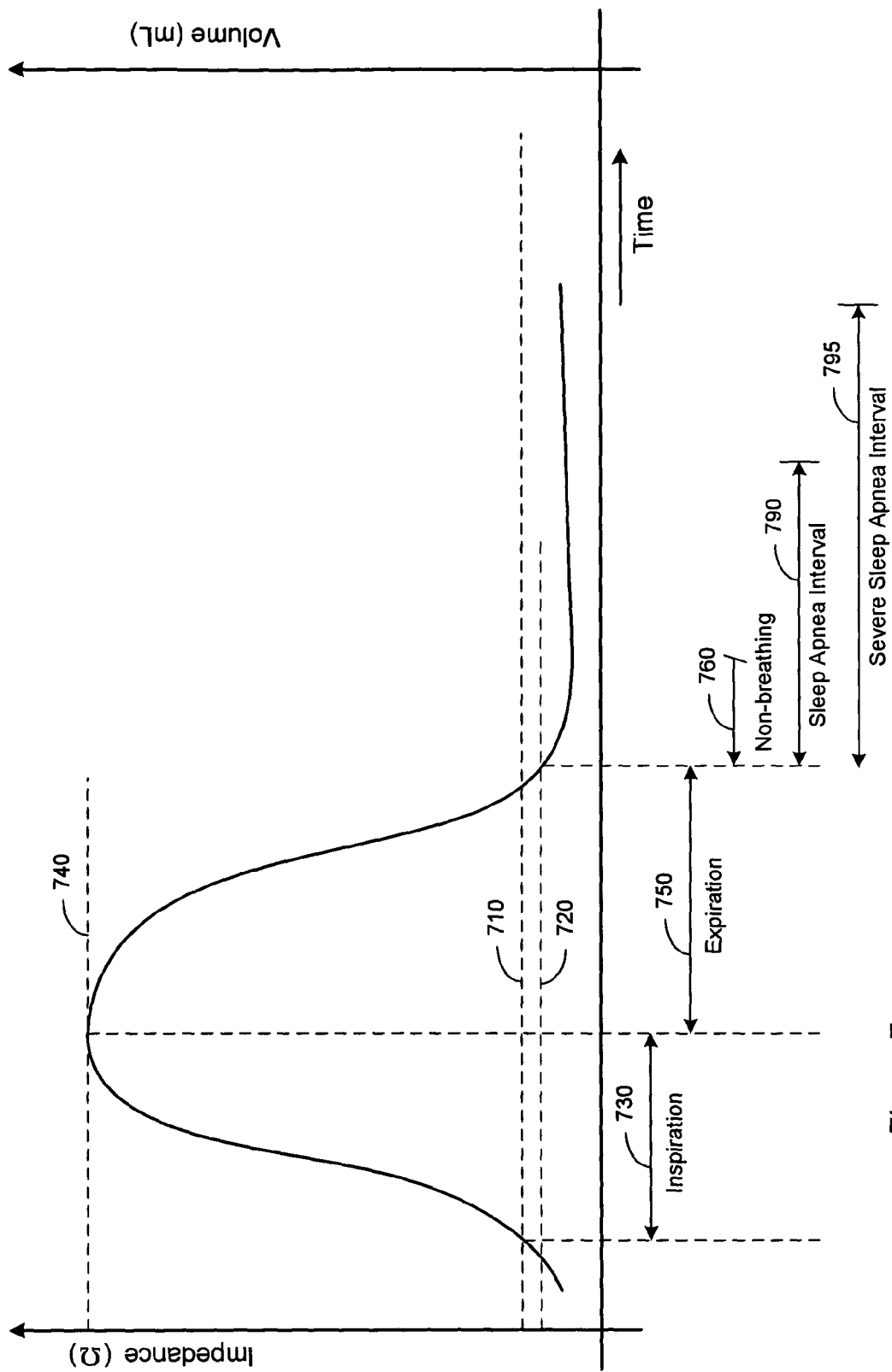
FIG. 7 illustrates respiration intervals used in detection of sleep apnea and severe sleep apnea according to embodiments of the invention.

Detection of sleep apnea and severe sleep apnea according to embodiments of the invention is illustrated in FIG. 7. The patient's respiration signals are monitored and the respiration cycles are defined according to inspiration 730, expiration 750, and non-breathing 760 intervals as described in connection with FIG. 6. A condition of sleep apnea is detected when a non-breathing period 760 exceeds a first predetermined interval 790, denoted the sleep apnea interval. A condition of severe sleep apnea is detected when the non-breathing period 760 exceeds a second predetermined interval 795, denoted the severe sleep apnea interval. For example, sleep apnea may be detected when the non-breathing interval exceeds about 10 seconds, and severe sleep apnea may be detected when the non-breathing interval exceeds about 20 seconds.

Figure 8A:
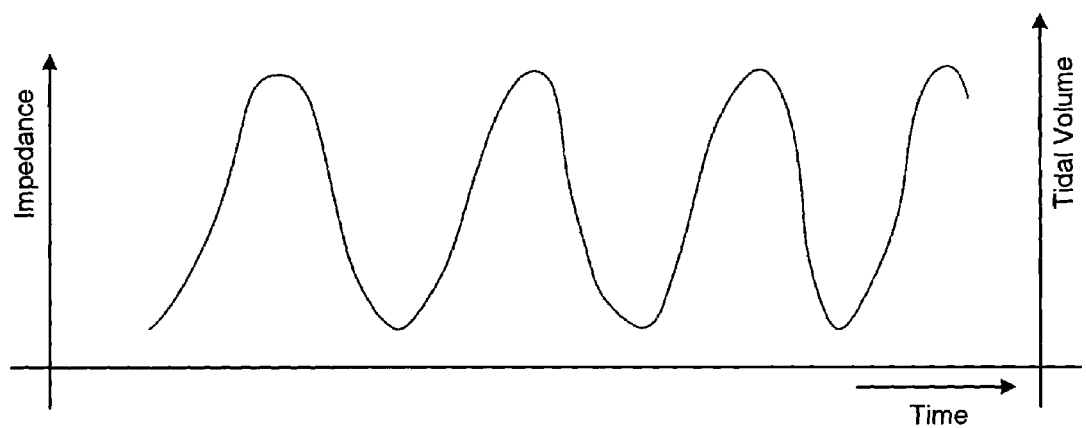
FIGS. 8A-B are graphs of tidal volume derived from transthoracic impedance measurements according to embodiments of the invention.
Figure 8B:
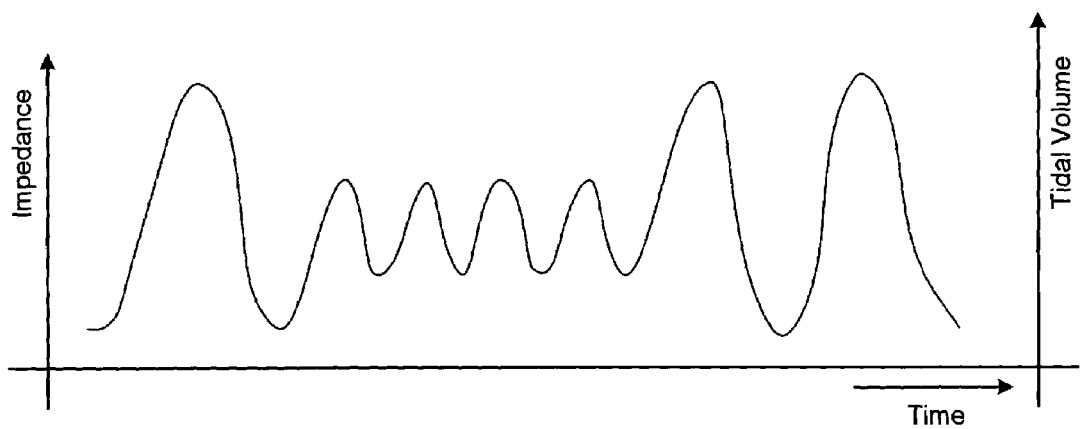

Hypopnea is a condition of disordered breathing characterized by abnormally shallow breathing. FIGS. 8A-B are graphs of tidal volume derived from transthoracic impedance measurements. The graphs compare the tidal volume of a normal breathing cycle to the tidal volume of a hypopnea episode. FIG. 8A illustrates normal respiration tidal volume and rate. As shown in FIG. 8B, hypopnea involves a period of abnormally shallow respiration.

According to an embodiment of the invention, hypopnea is detected by comparing a patient's respiratory tidal volume to a hypopnea tidal volume threshold. The tidal volume for each respiration cycle is derived from transthoracic impedance measurements acquired in the manner described above. The hypopnea tidal volume threshold may be established using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

Figure 9:
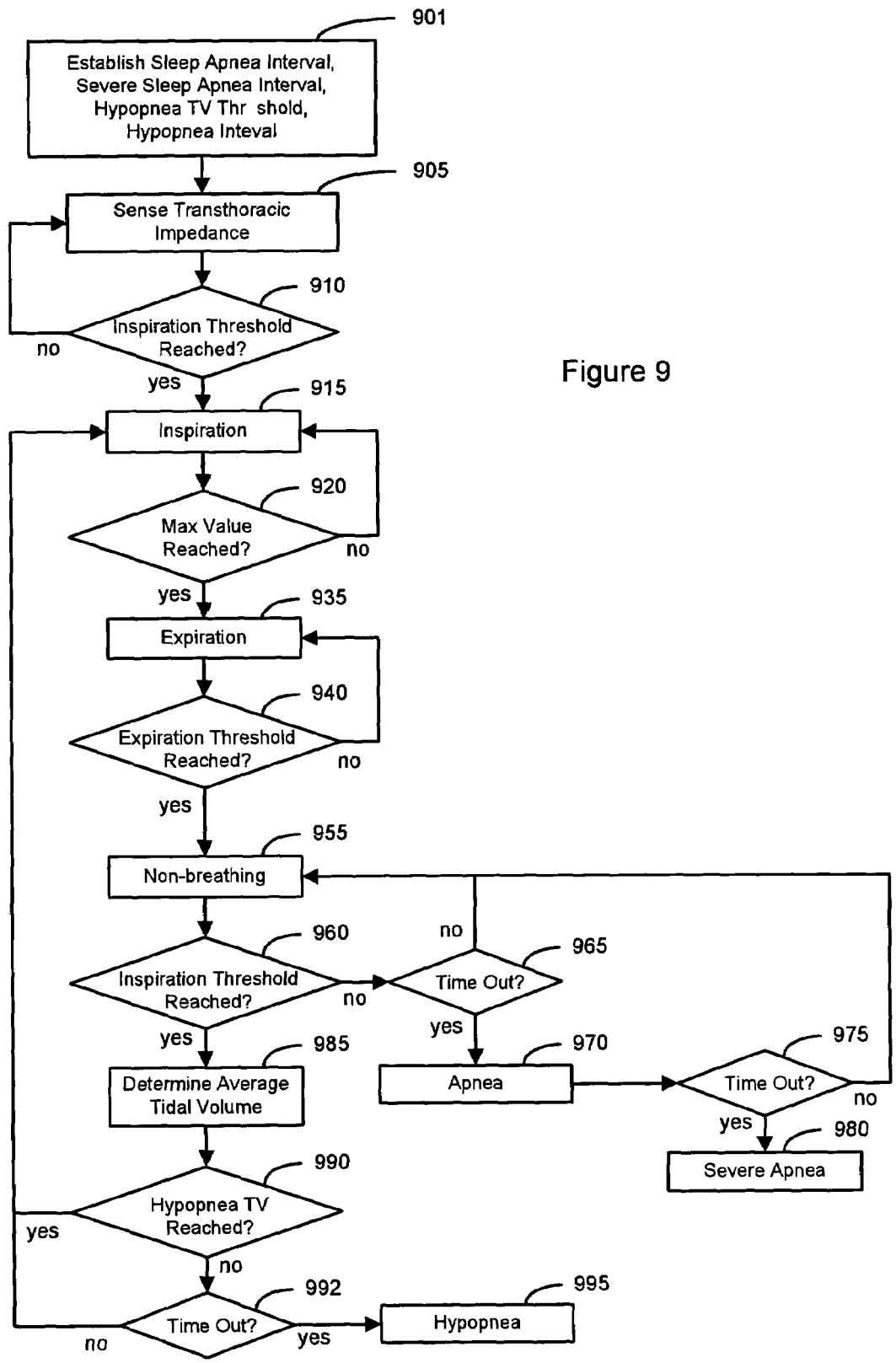
FIG. 9 is a flow chart illustrating a method of apnea and hypopnea detection according to embodiments of the invention.

FIG. 9 is a flow chart illustrating a method of apnea and/or hypopnea detection according to embodiments of the invention. Various parameters are established 901 before analyzing the patient's respiration for disordered breathing episodes, including, for example, inspiration and expiration thresholds, sleep apnea interval, severe sleep apnea interval, and hypopnea tidal volume threshold.

The patient's transthoracic impedance is measured 905 as described in more detail above. If the transthoracic impedance exceeds 910 the inspiration threshold, the beginning of an inspiration interval is detected 915. If the transthoracic impedance remains below 910 the inspiration threshold, then the impedance signal is checked 905 periodically until inspiration 915 occurs.

During the inspiration interval, the patient's transthoracic impedance is monitored until a maximum value of the transthoracic impedance is detected 920. Detection of the maximum value signals an end of the inspiration period and a beginning of an expiration period 935.

The expiration interval is characterized by decreasing transthoracic impedance. When the transthoracic impedance falls 940 below the expiration threshold, a non-breathing interval is detected 955.

If the transthoracic impedance does not exceed 960 the inspiration threshold within a first predetermined interval 965, denoted the sleep apnea interval, then a condition of sleep apnea is detected 970. Severe sleep apnea is detected 980 if the non-breathing period extends beyond a second predetermined interval 975, denoted the severe sleep apnea interval.

When the transthoracic impedance exceeds 960 the inspiration threshold, the tidal volume from the peak-to-peak transthoracic impedance is calculated, along with a moving average of past tidal volumes 985. The peak-to-peak transthoracic impedance provides a value proportional to the tidal volume of the respiration cycle. This value is compared 990 to a hypopnea tidal volume threshold. If the peak-to-peak transthoracic impedance is consistent with 990 the hypopnea tidal volume threshold for a predetermined time 992, then a hypopnea cycle is detected 995.

Additional sensors, such as motion sensors and/or posture sensors, may be used to confirm or verify the detection of a sleep apnea or hypopnea episode. The additional sensors may be employed to prevent false or missed detections of sleep apnea/hypopnea due to posture and/or motion related artifacts.

Another embodiment of the invention involves classifying respiration patterns as disordered breathing episodes based on the breath intervals and/or tidal volumes of one or more respiration cycles within the respiration patterns. According to this embodiment, the duration and tidal volumes associated with a respiration pattern are compared to duration and tidal volume thresholds. The respiration pattern is detected as a disordered breathing episode based on the comparison.

Figure 10:
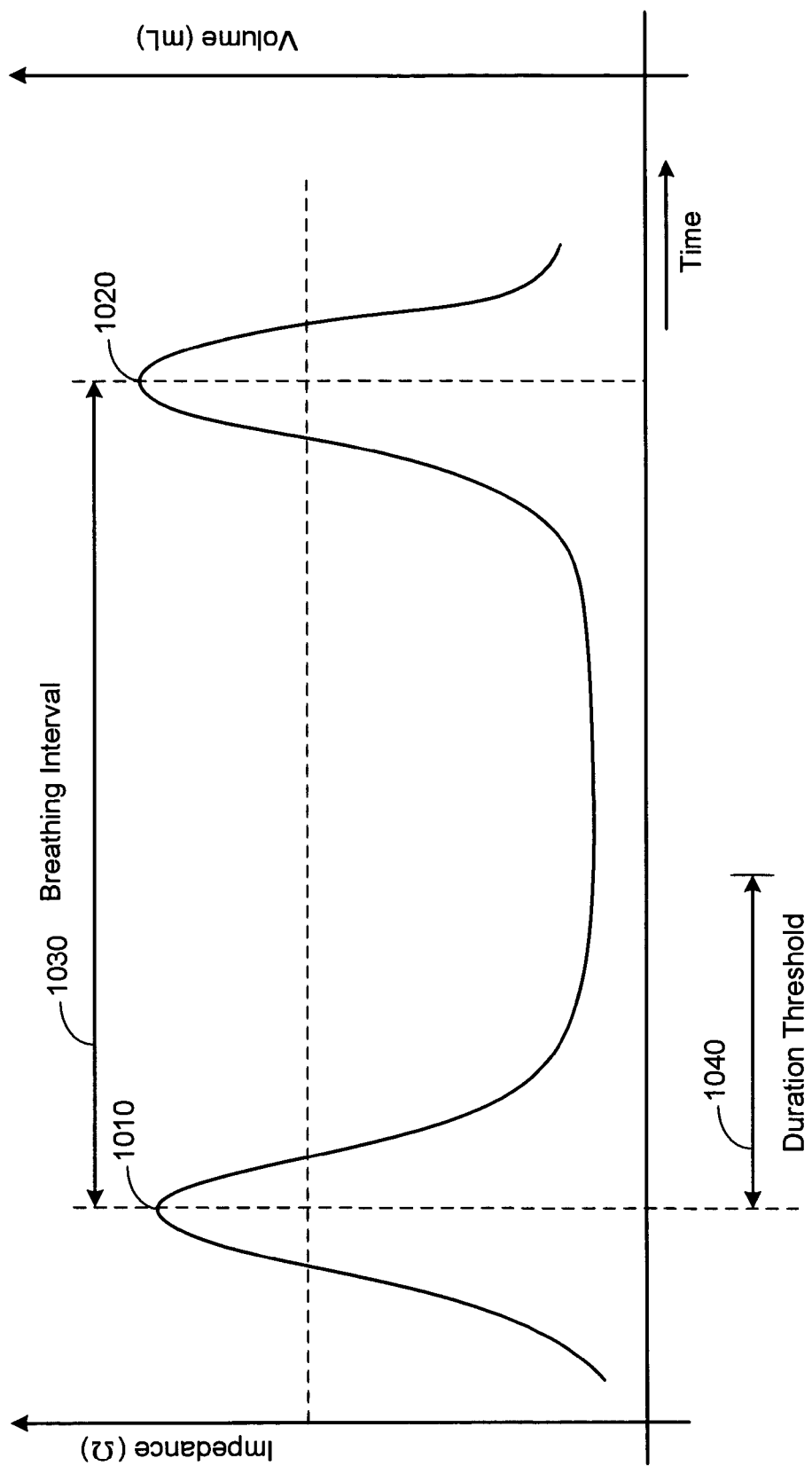
FIG. 10 is a graph illustrating a breathing interval according to embodiments of the invention.

According to principles of the invention, a breath interval is established for each respiration cycle. A breath interval represents the interval of time between successive breaths, as illustrated in FIG. 10. A breath interval 1030 may be defined in a variety of ways, for example, as the interval of time between successive maxima 1010, 1020 of the impedance signal waveform.

Detection of disordered breathing, in accordance with embodiments of the invention, involves the establishment of a duration threshold and a tidal volume threshold. If a breath interval exceeds the duration threshold, an apnea event is detected. Detection of sleep apnea, in accordance with this embodiment, is illustrated in the graph of FIG. 10. Apnea represents a period of non-breathing. A breath interval 1030 exceeding a duration threshold 1040, comprises an apnea episode.

Hypopnea may be detected using the duration threshold and tidal volume threshold. A hypopnea event represents a period of shallow breathing. Each respiration cycle in a hypopnea event is characterized by a tidal volume less than the tidal volume threshold. Further, the hypopnea event involves a period of shallow breathing greater than the duration threshold.

Figure 11:
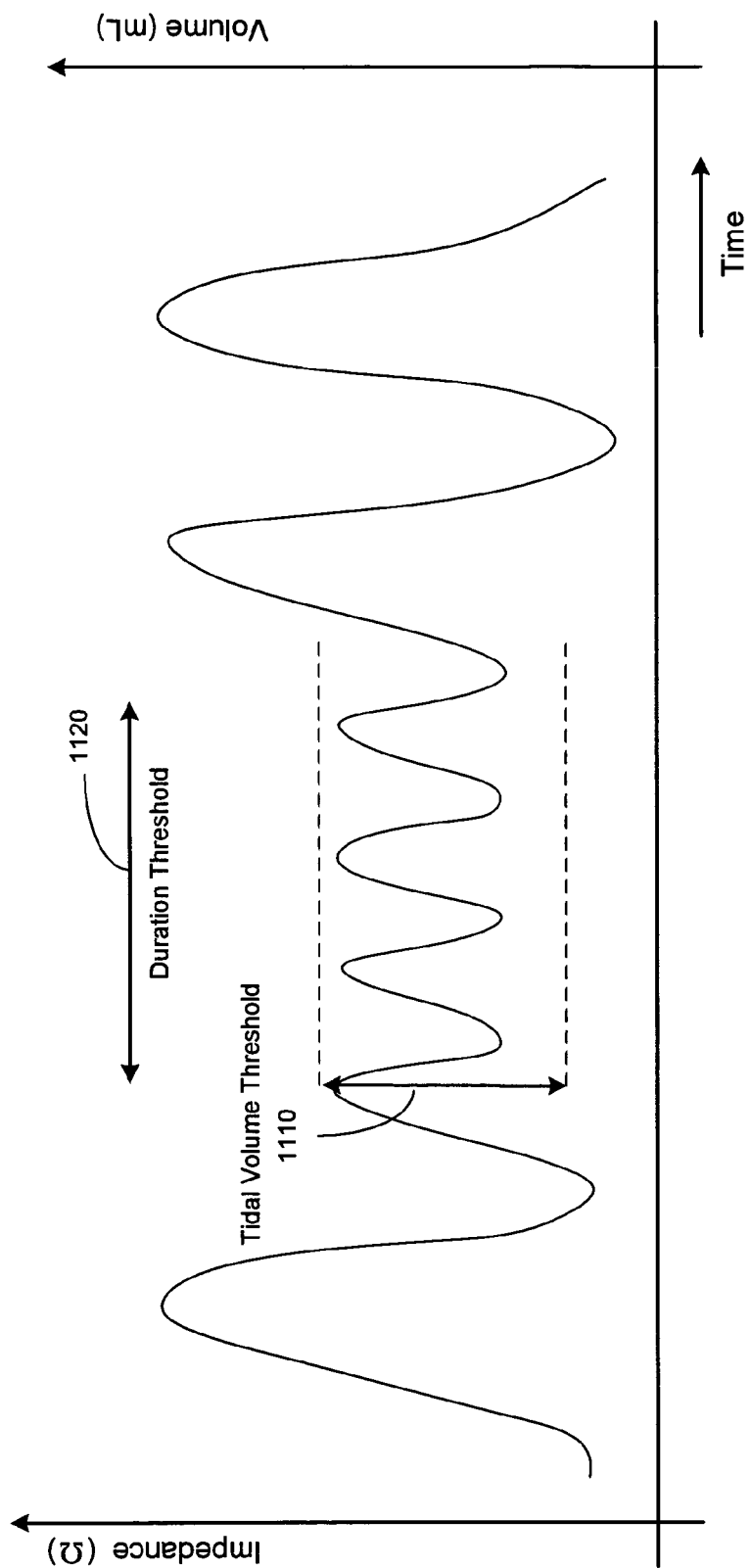
FIG. 11 is a graph illustrating a hypopnea detection approach in accordance with embodiments of the invention.

A hypopnea detection approach, in accordance with embodiments of the invention, is illustrated in FIG. 11. Shallow breathing is detected when the tidal volume of one or more breaths is below a tidal volume threshold 1110. If the shallow breathing continues for an interval greater than a duration threshold 1120, then the breathing pattern represented by the sequence of shallow respiration cycles, is classified as a hypopnea event.

Figure 12:
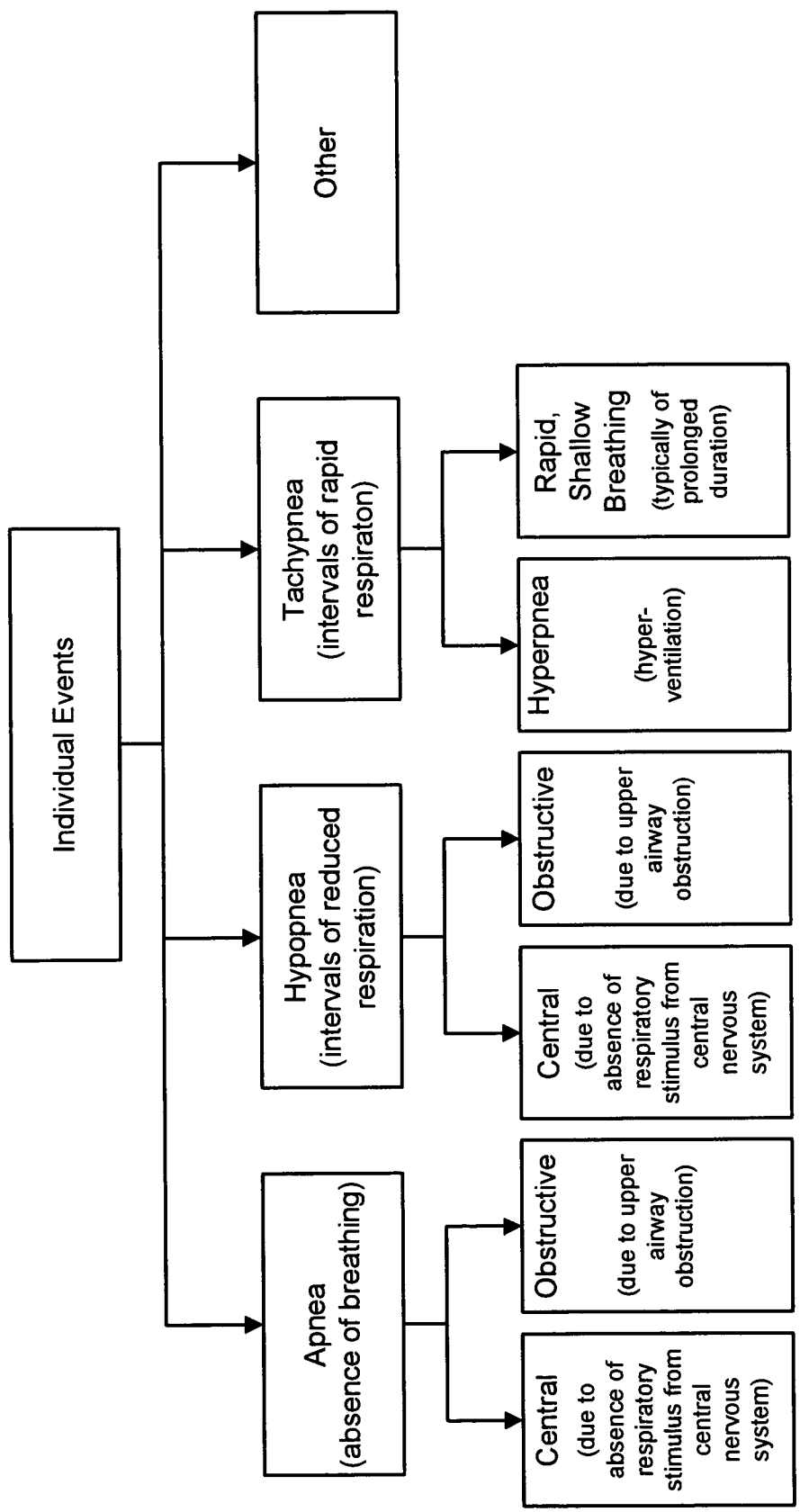
FIGS. 12-13 are charts illustrating nomenclature for individual disordered breathing events and combinations of disordered breathing events that can be addressed in accordance with embodiments of the invention, respectively.
Figure 13:
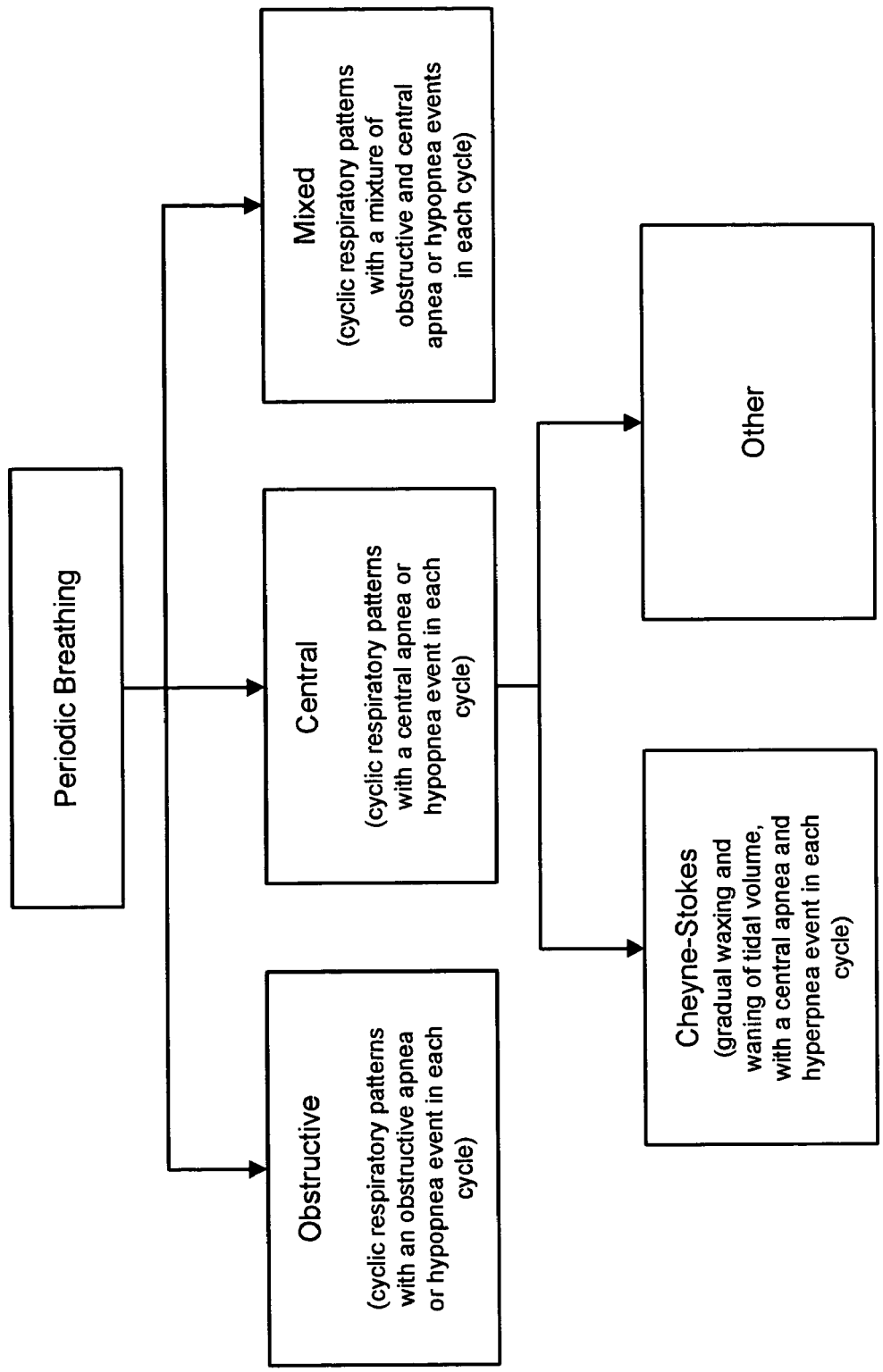

FIGS. 12 and 13 provide charts illustrating classification of individual disordered breathing events and series of periodically recurring disordered breathing events, respectively. As illustrated in FIG. 12, individual disordered breathing events may be grouped into apnea, hypopnea, tachypnea and other disordered breathing events. Apnea events are characterized by an absence of breathing. Intervals of reduced respiration are classified as hypopnea events. Tachypnea events include intervals of rapid respiration characterized by an elevated respiration rate.

As illustrated in FIG. 12, apnea and hypopnea events may be further subdivided as either central events, related to central nervous system dysfunction, or obstructive events, caused by upper airway obstruction. A tachypnea event may be further classified as a hyperpnea event, represented by hyperventilation, i.e., rapid deep breathing. A tachypnea event may alternatively be classified as rapid breathing, typically of prolonged duration.

FIG. 13 illustrates classification of combinations of periodically recurring disordered breathing events. Periodic breathing may be classified as obstructive, central or mixed. Obstructive periodic breathing is characterized by cyclic respiratory patterns with an obstructive apnea or hypopnea event in each cycle. Central periodic breathing involves cyclic respiratory patterns including a central apnea or hypopnea event in each cycle. Periodic breathing may also be of mixed origin. Mixed origin periodic breathing is characterized by cyclic respiratory patterns having a mixture of obstructive and central apnea events in each cycle. Cheyne-Stokes is a particular type of periodic breathing involving a gradual waxing and waning of tidal volume and having a central apnea and hyperpnea event in each cycle. Other manifestations of periodic breathing are also possible. Disordered breathing episodes may be classified based on the characteristic respiration patterns associated with particular types of disordered breathing.

Figures 14A, 14B, 14C, 14D, 14E:
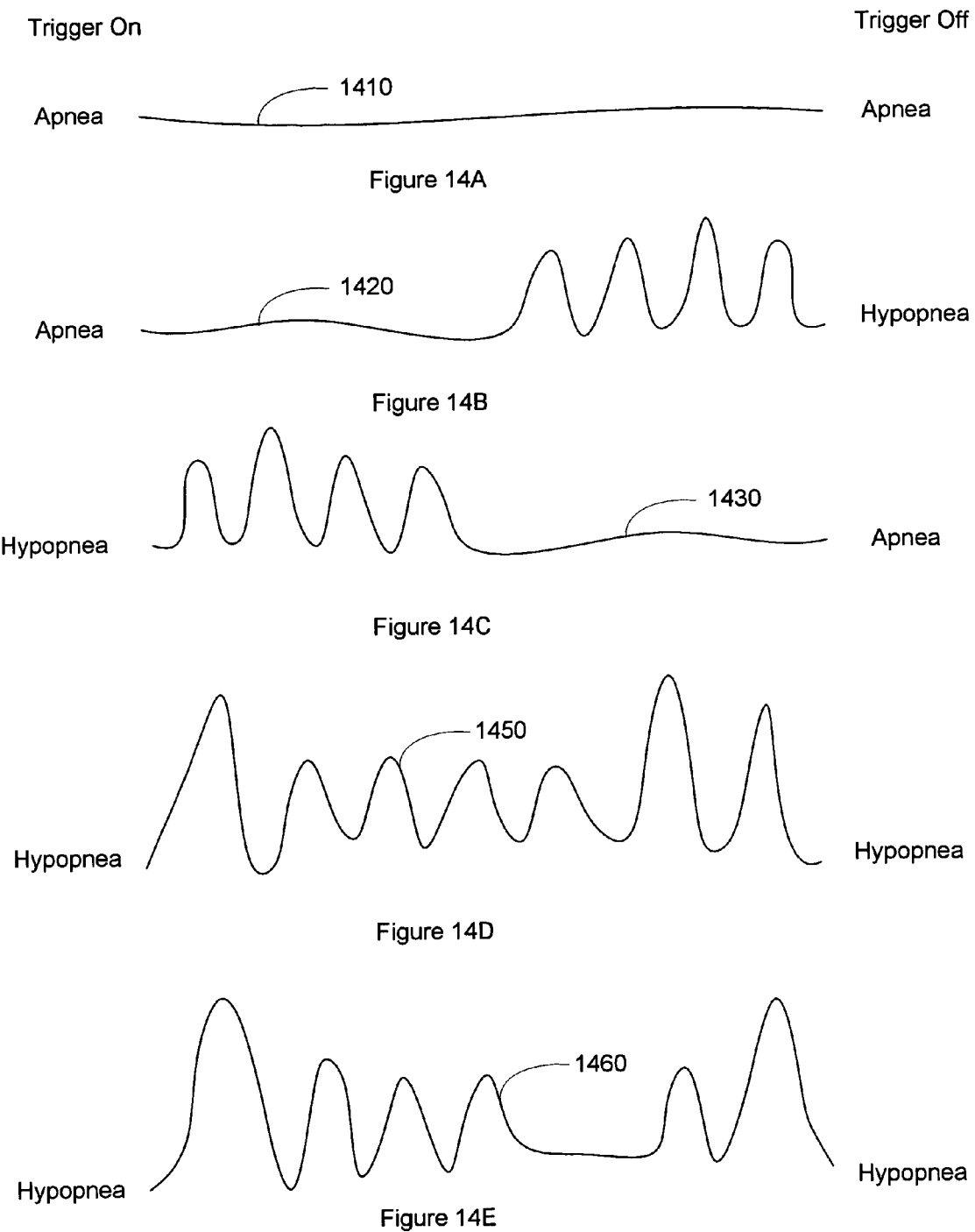
FIGS. 14A-14E are graphs illustrating disordered breathing events comprising a mixture of apnea and hypopnea respiration cycles.

As illustrated in FIGS. 14A-E, a respiration pattern detected as a disordered breathing episode may include only an apnea respiration cycle 1410 (FIG. 14A), only hypopnea respiration cycles 1450 (FIG. 14D), or a mixture of hypopnea and apnea respiration cycles 1420 (FIG. 14B), 1430 (FIG. 14C), 1460 (FIG. 14E). A disordered breathing event 1420 may begin with an apnea respiration cycle and end with one or more hypopnea cycles. In another pattern, the disordered breathing event 1430 may begin with hypopnea cycles and end with an apnea cycle. In yet another pattern, a disordered breathing event 1460 may begin and end with hypopnea cycles with an apnea cycle in between the hypopnea cycles.

Figure 15:
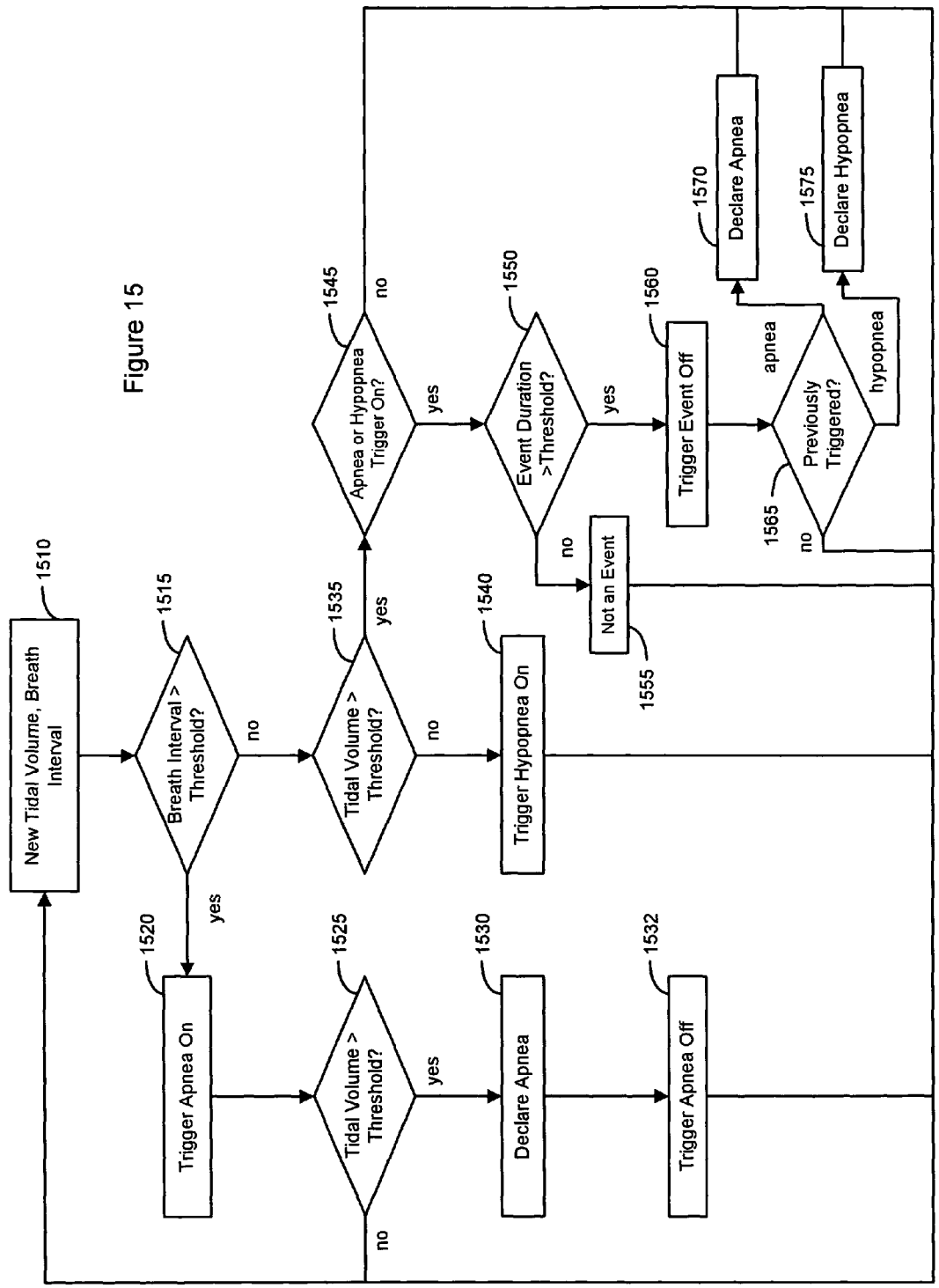
FIG. 15 is a flow graph of a method for detecting disordered breathing in accordance with an embodiment of the invention.

FIG. 15 is a flow graph of a method for detecting disordered breathing in accordance with embodiments of the invention. The method illustrated in FIG. 15 operates by classifying breathing patterns using breath intervals in conjunction with tidal volume and duration thresholds as previously described above. In this example, a duration threshold and a tidal volume threshold are established for determining both apnea and hypopnea breath intervals. An apnea episode is detected if the breath interval exceeds the duration threshold. A hypopnea episode is detected if the tidal volume of successive breaths remains less than the tidal volume threshold for a period in excess of the duration threshold. Mixed apnea/hypopnea episodes may also occur. In these cases, the period of disordered breathing is characterized by shallow breaths or non-breathing intervals. During the mixed apnea/hypopnea episodes, the tidal volume of each breath remains less than the tidal volume threshold for a period exceeding the duration threshold.

Transthoracic impedance is sensed and used to determine the patient's respiration cycles. Each breath 1510 may be characterized by a breath interval, the interval of time between two impedance signal maxima, and a tidal volume (TV).

If a breath interval exceeds 1515 the duration threshold, then the respiration pattern is consistent with an apnea event, and an apnea event trigger is turned on 1520. If the tidal volume of the breath interval exceeds 1525 the tidal volume threshold, then the breathing pattern is characterized by two respiration cycles of normal volume separated by a non-breathing interval. This pattern represents a purely apneic disordered breathing event, and apnea is detected 1530. Because the final breath of the breath interval was normal, the apnea event trigger is turned off 1532, signaling the end of the disordered breathing episode. However, if the tidal volume of the breath interval does not exceed 1525 the tidal volume threshold, the disordered breathing period is continuing and the next breath is checked 1510.

If the breath interval does not exceed 1515 the duration threshold, then the tidal volume of the breath is checked 1535. If the tidal volume does not exceed 1535 the tidal volume threshold, the breathing pattern is consistent with a hypopnea cycle and a hypopnea event trigger is set on 1540. If the tidal volume exceeds the tidal volume threshold, then the breath is normal.

If a period of disordered breathing is in progress, detection of a normal breath signals the end of the disordered breathing. If disordered breathing was previously detected 1545, and if the disordered breathing event duration has not exceeded 1550 the duration threshold, and the current breath is normal, then no disordered breathing event is detected 1555. If disordered breathing was previously detected 1545, and if the disordered breathing event duration has extended for a period of time exceeding 1550 the duration threshold, and the current breath is normal, then the disordered breathing trigger is turned off 1560. In this situation, the duration of the disordered breathing episode was of sufficient duration to be classified as a disordered breathing episode. If an apnea event was previously triggered 1565, then an apnea event is declared 1570. If a hypopnea was previously triggered 1565, then a hypopnea event is declared 1575.

Figure 16:
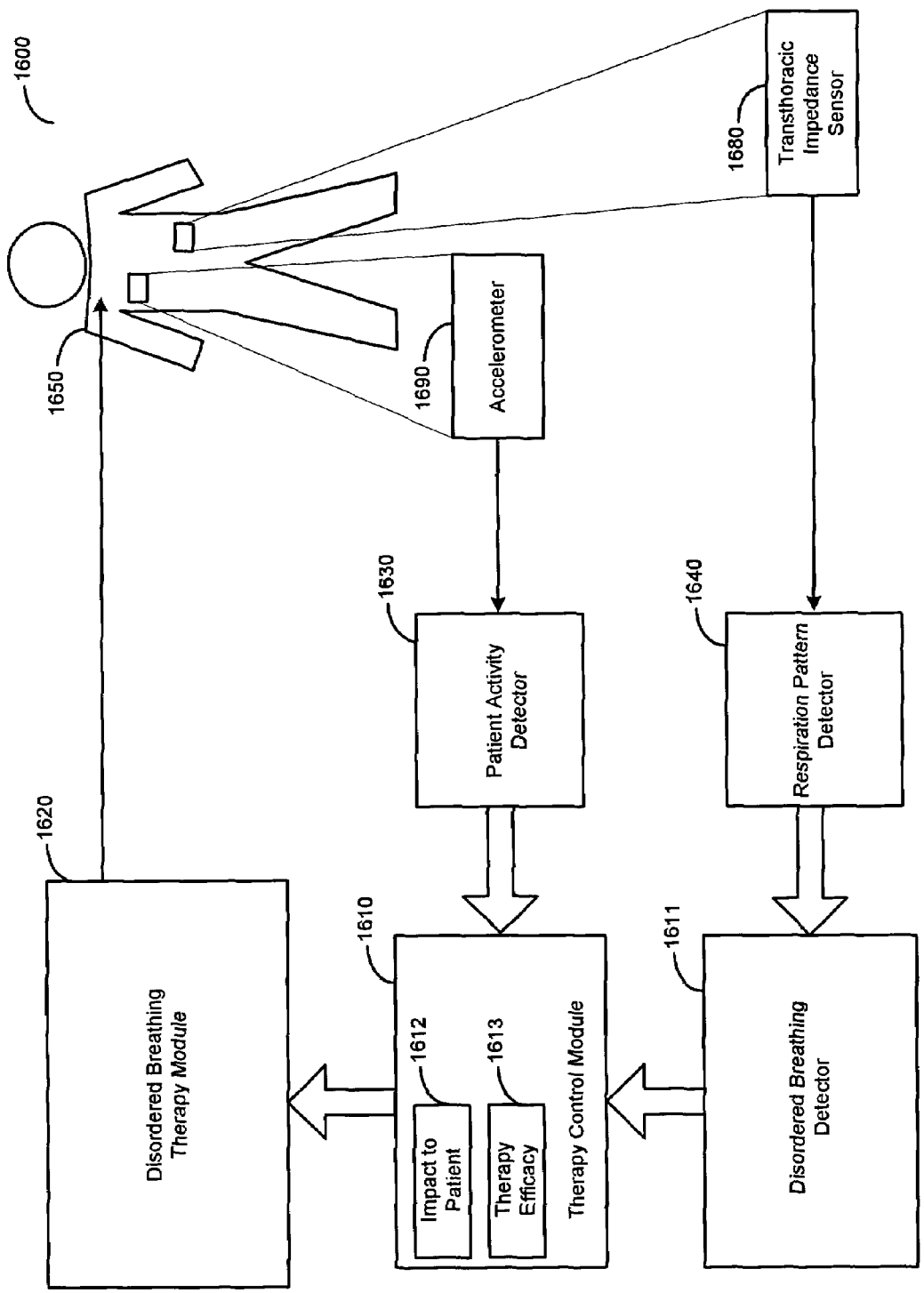
FIG. 16 is a block diagram of a sleep-disordered breathing therapy system in accordance with an embodiment of the invention.

FIG. 16 is a block diagram of a sleep-disordered breathing therapy system 1600 arranged in accordance with embodiments of the invention. The therapy system 1600 includes a transthoracic impedance sensor 1680 that provides a signal associated with the respiration of a patient 1650. The output of the transthoracic impedance sensor is coupled to a respiration pattern detector 1640. The patient's respiration patterns are analyzed by a disordered breathing detector 1611 to detect sleep-disordered breathing as described in more detail above.

The sleep-disordered breathing detector 1611 is coupled to a therapy control module 1610. If sleep-disordered breathing is detected by the disordered breathing detector 1611, the therapy control module 1610 signals a therapy module 1620 to deliver disordered breathing therapy to the patient 1650. The therapy control module 1610 performs assessment of the therapy and adapts the therapy to enhance therapy efficacy, to deliver therapy that reduces an impact of the therapy on the patient, or to achieve a combination of these therapeutic goals.

The therapy control module 1620 may include, for example, circuitry 1613 for evaluating therapy efficacy and circuitry 1612 to assess the impact of the therapy on the patient. In one embodiment, the efficacy of the therapy is assessed by analyzing the patient's respiration patterns following therapy delivery to detect and classify further episodes of disordered breathing. If the disordered breathing episode continues, or if the severity of the disordered breathing is not sufficiently mitigated by the therapy, the therapy may be adapted by the therapy control module 1610 to provide a more effective therapy.

In another example implementation, the therapy may be adapted based on one or more of the acute and/or chronic physiological responses to disordered breathing as discussed above. For example, the therapy may be adapted based on a level of hypoxia, intrathoracic pressure, or heart rate surges experienced by the patient during or shortly after a disordered breathing episode. Further, therapy may be adapted based on various chronic conditions, including heart rate variability, or increases in blood pressure or sympathetic nerve activity. A number of chronic physiological responses to disordered breathing may be detected after termination of one or more disordered breathing episodes, e.g., during periods of wakefulness. Further, adaptation of the therapy may be accomplished based on a combination of acute and chronic effects.

One method of evaluating the impact of the therapy on the patient involves determining the number of arousals per hour experienced by the patient. In one example, an accelerometer 1690 coupled to a patient activity detector 1630 may be used to produce a signal indicative of patient activity. If the therapy is effective, but the number of arousals per hour experienced by the patient are unacceptably high, the therapy may be adapted by the therapy control module 1610 to reduce therapy impact.

Figure 17:
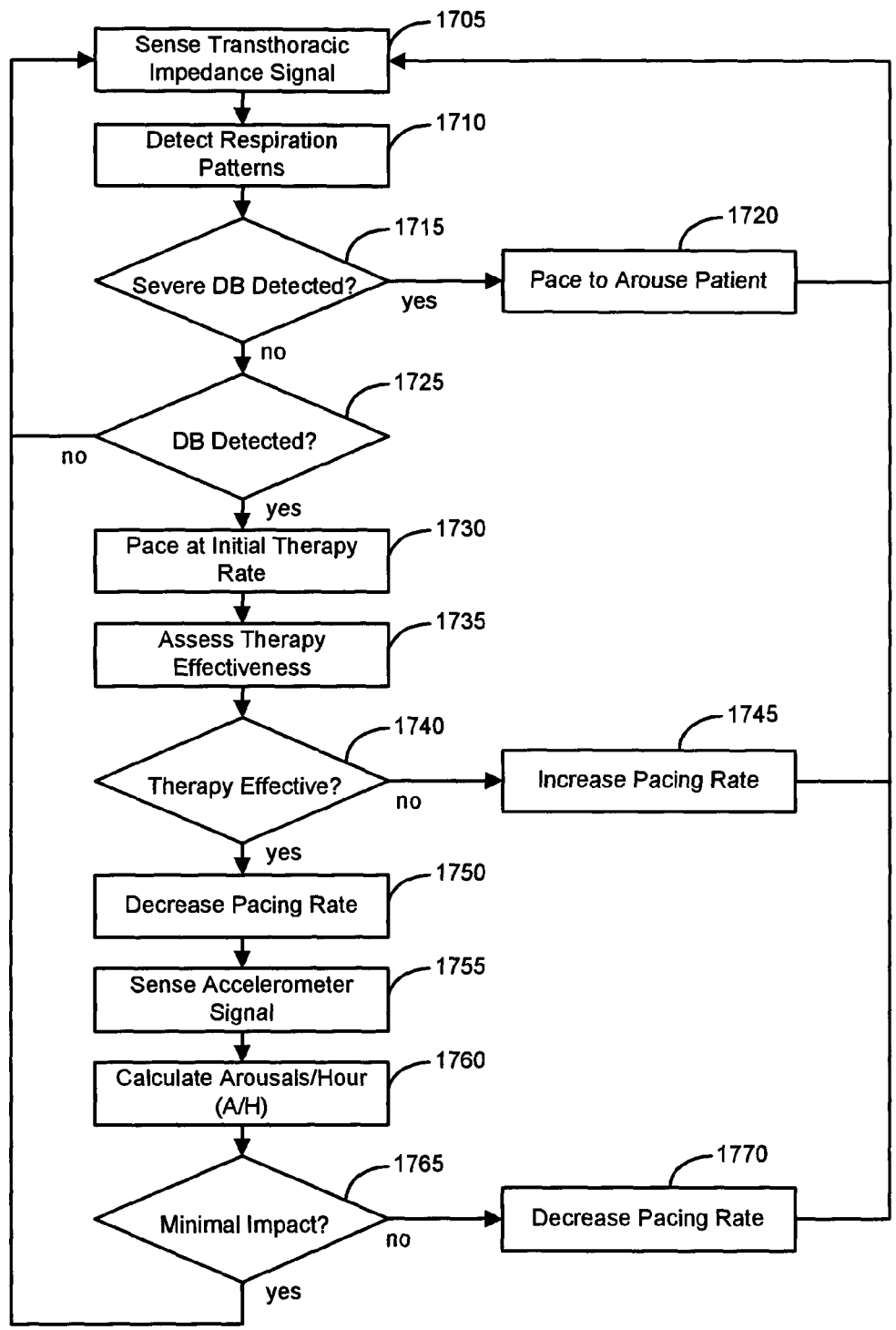
FIG. 17 is a flow graph of a method of adapting a therapy for disordered breathing in accordance with embodiments of the invention.

FIG. 17 is a flow graph illustrating a method for providing cardiac electrical therapy to mitigate sleep-disordered breathing according to embodiments of the invention. As described above in connection with the block diagram of FIG. 16, a transthoracic impedance sensor may be used to provide a signal characterizing the patient's respiration patterns. An accelerometer signal is used to assess therapy impact based on the number of arousals per hour experienced by the patient. More sensitive techniques for detecting arousals, e.g., EEG, may be used place of, or in addition to, the accelerometer method.

The signal from the transthoracic impedance sensor is sensed 1705 and used to detect 1710 the patient's respiration waveform patterns. If the patient's respiration patterns are consistent 1715 with severe disordered breathing (DB), cardiac therapy is delivered 1720 to the patient initially at a relatively aggressive level. In the case of cardiac electrical therapy involving pacing at a relatively high rate, the therapy may cause the patient to arouse from sleep, thereby terminating the severe disordered breathing episode. The cardiac electrical therapy may be modified over the course of the night to reduce the level of impact.

If the patient's respiration patterns do not indicate 1715 severe disordered breathing, but are consistent 1725 with disordered breathing (DB) respiration patterns, cardiac electrical therapy is delivered 1730 at an initial level, for example, at a pacing rate of about 5 to about 15 bpm above the patient's intrinsic rate or the patient's normal sleep rate.

The effectiveness of the therapy is evaluated 1735, for example, by analyzing the patient's respiration patterns to detect and assess further disordered breathing episodes, if any. If the therapy is not effective 1740, e.g., the disordered breathing continues or additional incidents of disordered breathing are detected, the therapy is modified 1745 by increasing the level of therapy by a predetermined amount, e.g., about 5 bpm for cardiac pacing therapy. If the therapy is effective 1740, the therapy level may be decreased 1750 by a predetermined amount, for example, about 5 bpm in the case of cardiac pacing therapy. The level of the adapted therapy may be constrained by upper and lower limits, e.g., upper and lower disordered breathing cardiac pacing therapy limits.

The impact of the therapy on the patient can be determined based on the patient's sleep quality. One measure of sleep quality involves calculating the number of arousals per hour experienced by the patient. During an arousal from sleep, the patient's activity increases. The level of patient activity may be detected by sensing 1755 an accelerometer signal responsive to patient movement, or by analyzing the patient's minute ventilation signal, or using a combination of accelerometer and minute ventilation signals. Based on the detected patient activity as indicated by the activity signals, the number of arousals experienced by the patient per hour (A/H) may be calculated 1760. If the number of arousals per hour experienced by the patient is below a predetermined threshold, then the patient's sleep quality is acceptable, and the impact 1765 of the therapy is determined to be acceptable. If the therapy impact is determined to be acceptable 1765, the therapy level is not modified. If the number of arousals per hour exceeds the threshold, then the impact 1765 of the therapy is not acceptable and the therapy level, for example, the pacing rate, may be decreased 1770.

It is understood that the components and functionality depicted in the figures and described herein can be implemented in hardware, software, or a combination of hardware and software. It is further understood that the components and functionality depicted as separate or discrete blocks/elements in the figures can be implemented in combination with other components and functionality, and that the depiction of such components and functionality in individual or integral form is for purposes of clarity of explanation, and not of limitation.

The following commonly owned U.S. patents applications, some of which have been identified above, are hereby incorporated by reference in their respective entireties: U.S. Pat. No. 7,252,640, U.S. Pat. No. 7,189,204, U.S. Publication No. 2005/0042589 concurrently filed with this patent application, U.S. Pat. No. 7,396,333 filed concurrently with this patent application, U.S. Publication No. 2005/0043652 filed concurrently with this patent application, and U.S. Pat. No. 7,680,537 filed concurrently with this patent application.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A medical device, comprising:
   a detector system configured to detect patient conditions;
   a disordered breathing detection system coupled to the detector system and configured to detect disordered breathing;
   a therapy control system coupled to the disordered breathing detection system and the detector system configured to deliver a cardiac electrical therapy to mitigate the disordered breathing, the therapy control system comprising:
      circuitry configured to assess an efficacy of the therapy based on one or more first conditions of the detected patient conditions; and
      circuitry configured to assess a negative impact of the therapy on a patient based on one or more second conditions of the detected patient conditions, the one or more first conditions differing from the one or more second conditions at least in part,
      wherein the therapy control system is configured to adapt the cardiac electrical therapy to promote the therapy efficacy and adapt the cardiac electrical therapy to reduce the negative impact of the therapy on the patient; and
   a therapy delivery system coupled to the therapy control system and configured to deliver the adapted therapy to the patient, wherein at least one of the detector system, the disordered breathing detection system, the therapy control system, and the therapy delivery system includes an implantable component.

2. The medical device of claim 1, wherein at least two of the detector system, the disordered breathing detection system, the therapy control system, and the therapy delivery system include implantable components.

3. The medical device of claim 1, wherein at least three of the detector system, the disordered breathing detection system, the therapy control system, and the therapy delivery system include implantable components.

4. The medical device of claim 1, wherein each of the detector system, the disordered breathing detection system, the therapy control system, and the therapy delivery system include implantable components.

5. The medical device of claim 1, wherein the detector system comprises a patient-internal sensor.

6. The medical device of claim 1, wherein the detector system comprises a patient-external sensor.

7. The medical device of claim 1, wherein the detector system comprises a patient input device.

8. The medical device of claim 1, wherein at least one of the detector system, the disordered breathing detection system, the therapy control system, and the therapy delivery system includes a wirelessly connected component.

9. The medical device of claim 1, wherein the disordered breathing detection system is configured to detect a respiration pattern of one or more respiration cycles, determine one or more characteristics of the respiration pattern, and classify the respiration pattern as disordered breathing based on the one or more characteristics of the respiration pattern.

10. The medical device of claim 1, wherein the therapy control system is configured to adapt the therapy based on patient comfort.

11. The medical device of claim 1, wherein the therapy control system is configured to adapt the therapy based on sleep quality.

12. The medical device of claim 1, wherein the therapy control system is configured to adapt the therapy based on respiration quality.

13. The medical device of claim 1, wherein the therapy control system is configured to adapt the therapy to increase a lifetime of the medical device.

14. The medical device of claim 1, wherein the therapy control system is configured to adapt the therapy to reduce interaction between a therapy to treat a cardiac disorder and the therapy to mitigate the disordered breathing.

15. The medical device of claim 1, wherein the therapy control system is configured to adapt the therapy to a more aggressive therapy if an initial therapy is ineffective.

16. The medical device of claim 1, wherein the therapy control system is configured to adapt the therapy to a less aggressive therapy if an initial therapy is effective.

17. The medical device of claim 1, wherein the therapy control system is configured to adapt the therapy to a less aggressive therapy if an initial therapy does not reduce the impact of the therapy on the patient.

18. The medical device of claim 1, wherein the therapy control system is configured to adapt the therapy by modifying a pacing regimen.

19. The medical device of claim 1, wherein the therapy control system is configured to adapt the therapy by adjusting a pacing rate.

20. The medical device of claim 1, wherein the therapy control system is configured to adapt the therapy by adjusting a pacing energy.

21. The medical device of claim 1, wherein the therapy control system is configured to adapt the therapy by adjusting a pacing mode.

22. The medical device of claim 1, wherein the therapy control system is configured to adapt the therapy by adjusting a pacing site.

23. The medical device of claim 1, wherein the therapy control system is configured to adapt the therapy to mitigate apnea.

24. The medical device of claim 1, wherein the therapy control system is configured to adapt the therapy to mitigate hypopnea.

25. The medical device of claim 1, wherein the therapy control system is configured to adapt the therapy to mitigate Cheyne-Stokes respiration.

26. The medical device of claim 1, wherein the therapy control system is configured to adapt the therapy to mitigate sleep-disordered breathing.

27. The medical device of claim 1, wherein the therapy delivery system is configured to deliver bi-ventricular pacing therapy.

28. The medical device of claim 1, wherein the therapy delivery system is configured to deliver atrial pacing.

29. The medical device of claim 1, wherein the therapy delivery system is configured to deliver ventricular pacing.

30. The medical device of claim 1, wherein the therapy delivery system is configured to deliver multi-chamber pacing.

31. The medical device of claim 1, wherein the therapy delivery system is configured to deliver multi-site pacing.

32. A medical device, comprising:
   a detector system configured to detect patient conditions;
   a disordered breathing detection system coupled to the detector system and configured to detect disordered breathing;
   a therapy control system coupled to the disordered breathing detection system and the detector system configured to deliver a cardiac electrical therapy to mitigate the disordered breathing, the therapy control system comprising circuitry configured to assess a negative impact of the therapy on a patient based on at least one first condition of the detected patient conditions other than sleep fragmentation, the therapy control system configured to adapt the cardiac electrical therapy to reduce the negative impact of the therapy on the patient; and
   a therapy delivery system coupled to the therapy control system and configured to deliver the adapted therapy to the patient, wherein at least one of the detector system, the disordered breathing detection system, the therapy control system, and the therapy delivery system includes an implantable component.

33. The medical device of claim 32 wherein the therapy control system is configured to adapt the cardiac electrical therapy toward balancing the negative impact of the therapy with an efficacy of the therapy at mitigating the disordered breathing.

34. The medical device of claim 32 wherein the negative impact of the therapy comprises a decreased lifetime of the medical device.

35. The medical device of claim 32 wherein the negative impact of the therapy comprises stress on physiological systems.

36. The medical device of claim 32 wherein the negative impact of the therapy comprises patient discomfort.

37. The medical device of claim 32 wherein the negative impact of the therapy comprises interaction with cardiac pacing algorithms.

38. The medical device of claim 32 wherein the therapy control system is configured to adapt the cardiac electrical therapy to reduce the negative impact on sleep quality caused by the therapy.

* * * * *